US010307090B2

(12) United States Patent
Rudmann et al.

(10) Patent No.: US 10,307,090 B2
(45) Date of Patent: Jun. 4, 2019

(54) SENSOR FOR DETECTION OF GAS AND METHOD FOR DETECTION OF GAS

(71) Applicant: SENTEC AG, Therwil (CH)

(72) Inventors: Dominik Rudmann, Basel (CH); Peter Matthias Schumacher, Kirchlindach (CH); Joseph Lang, Ranspach le Haut (FR); Simon Caruel, Allschwil (CH); Christoph Ellenberger-Girard, Therwil (CH); Ross Stanley, Epalinges (CH); Rolf Eckert, Neuchâtel (CH); Branislav Timotijevic, Lausanne (CH); Maurizio Tormen, Peseux (CH)

(73) Assignee: SenTec AG, Therwil (CH)

( * ) Notice: Subject to any disclaimer, the term of this patent is extended or adjusted under 35 U.S.C. 154(b) by 544 days.

(21) Appl. No.: 14/906,669

(22) PCT Filed: Jul. 21, 2014

(86) PCT No.: PCT/EP2014/065645
§ 371 (c)(1),
(2) Date: Jan. 21, 2016

(87) PCT Pub. No.: WO2015/011103
PCT Pub. Date: Jan. 29, 2015

(65) Prior Publication Data
US 2016/0151009 A1    Jun. 2, 2016

(30) Foreign Application Priority Data

Jul. 22, 2013  (WO) ................ PCT/EP2013/065379

(51) Int. Cl.
*A61B 5/1455*   (2006.01)
*A61B 5/145*    (2006.01)
(Continued)

(52) U.S. Cl.
CPC ...... *A61B 5/14552* (2013.01); *A61B 5/14542* (2013.01); *G01N 21/03* (2013.01);
(Continued)

(58) Field of Classification Search
CPC .............. A61B 5/1455; A61B 5/14542; A61B 5/14551; A61B 5/14552; A61B 21/3504; A61B 21/03
See application file for complete search history.

(56) References Cited

U.S. PATENT DOCUMENTS 6,512,230 B1 *  1/2003  von Lerber ........ G01N 21/3504
                                                 250/339.13
7,164,812 B2    1/2007  Depeursinge et al.
(Continued)

FOREIGN PATENT DOCUMENTS

EP    1 969 997 A1    9/2008
JP    2010522868 A    7/2010
(Continued)

OTHER PUBLICATIONS

Rebecca L. Kozodoy et al., "Small-Bore Hollow Waveguide Infrared Absorption Cells for Gas Sensing", Applied Spectroscopy, Mar. 1996, vol. 50, No. 3, pp. 415-417.
(Continued)

*Primary Examiner* — Eric F Winakur
*Assistant Examiner* — Chu Chuan Liu
(74) *Attorney, Agent, or Firm* — Davis & Bujold PLLC; Michael J. Bujold

(57) ABSTRACT

A sensor (1) for detection of gas, in particular for detection of $CO_2$. The sensor (1) has a contact face (2) which can be directed towards a measuring site. The sensor (1) includes at least one radiation source (3), a measurement volume (4) for receiving the gas to be measured, and at least a first detector (5) for detection of radiation transmitted from the source (3)
(Continued)

Figure 1:
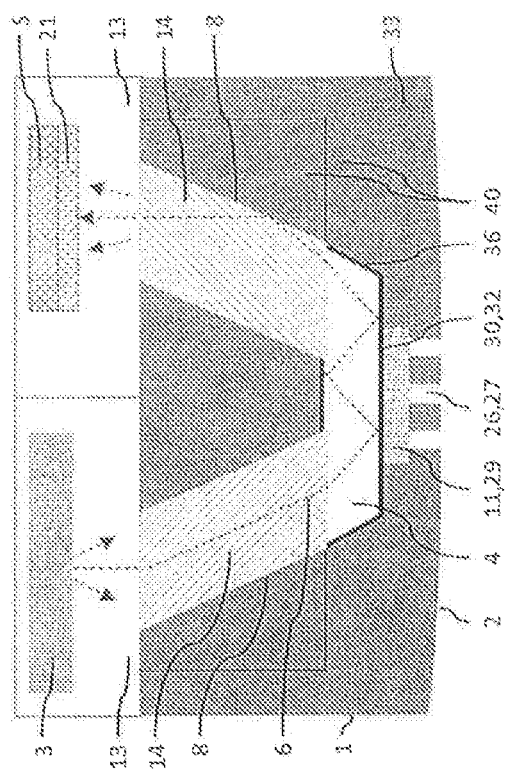

to the first detector (5) through the measurement volume (4). The sensor has a path (6) of the radiation between radiation source (3) and first detector (5). The radiation propagates along the path in a non-imaging way.

26 Claims, 20 Drawing Sheets

(51) Int. Cl.
 *G01N 33/49* (2006.01)
 *G01N 21/3504* (2014.01)
 *G01N 21/03* (2006.01)
 *G01N 33/497* (2006.01)

(52) U.S. Cl.
 CPC ....... *G01N 21/3504* (2013.01); *G01N 33/497* (2013.01); *G01N 33/4925* (2013.01); *G01N 2201/068* (2013.01)

(56) References Cited

U.S. PATENT DOCUMENTS

| | | | |
|---|---|---|---|
| 8,527,023 | B2 | 9/2013 | Hayoz et al. |
| 9,035,256 | B2 | 5/2015 | Gibson et al. |
| 2006/0151723 | A1* | 7/2006 | Arndt ................. G01J 3/108 250/504 R |
| 2007/0063125 | A1* | 3/2007 | Downing, Jr. .......... G01J 1/02 250/205 |
| 2008/0231857 | A1 | 9/2008 | Depeursinge et al. |
| 2014/0303462 | A1 | 10/2014 | Ellenberger-Girard et al. |

FOREIGN PATENT DOCUMENTS

| | | |
|---|---|---|
| JP | 2013517467 A | 5/2013 |
| WO | 2004/017054 A1 | 2/2004 |
| WO | 2008/110927 A2 | 9/2008 |
| WO | 2008/132205 A1 | 11/2008 |
| WO | 2013/064313 A1 | 5/2013 |

OTHER PUBLICATIONS

International Search Report issued in corresponding PCT application No. PCT/EP2014/065645 dated Oct. 8, 2014.

Written Opinion issued in corresponding PCT application No. PCT/EP2014/065645 dated Oct. 8, 2014.

Japanese Office Action issued in corresponding Japanese Patent Application No. 2016-528488 dated Jul. 3, 2018.

* cited by examiner

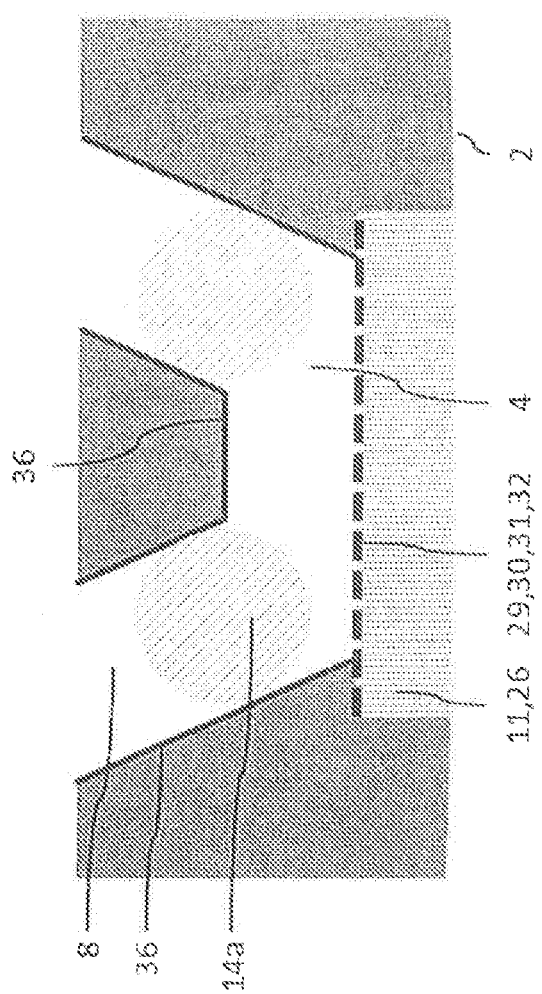

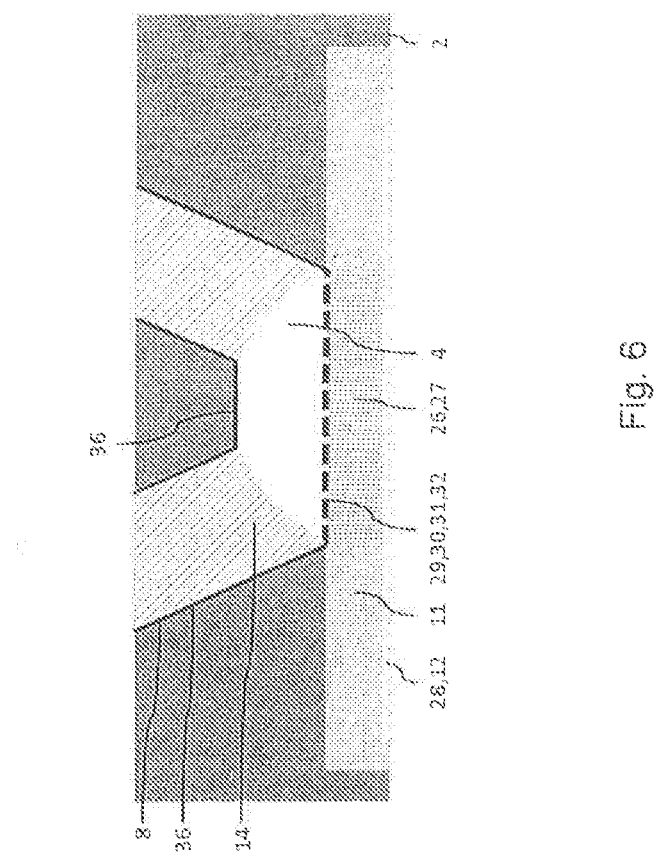

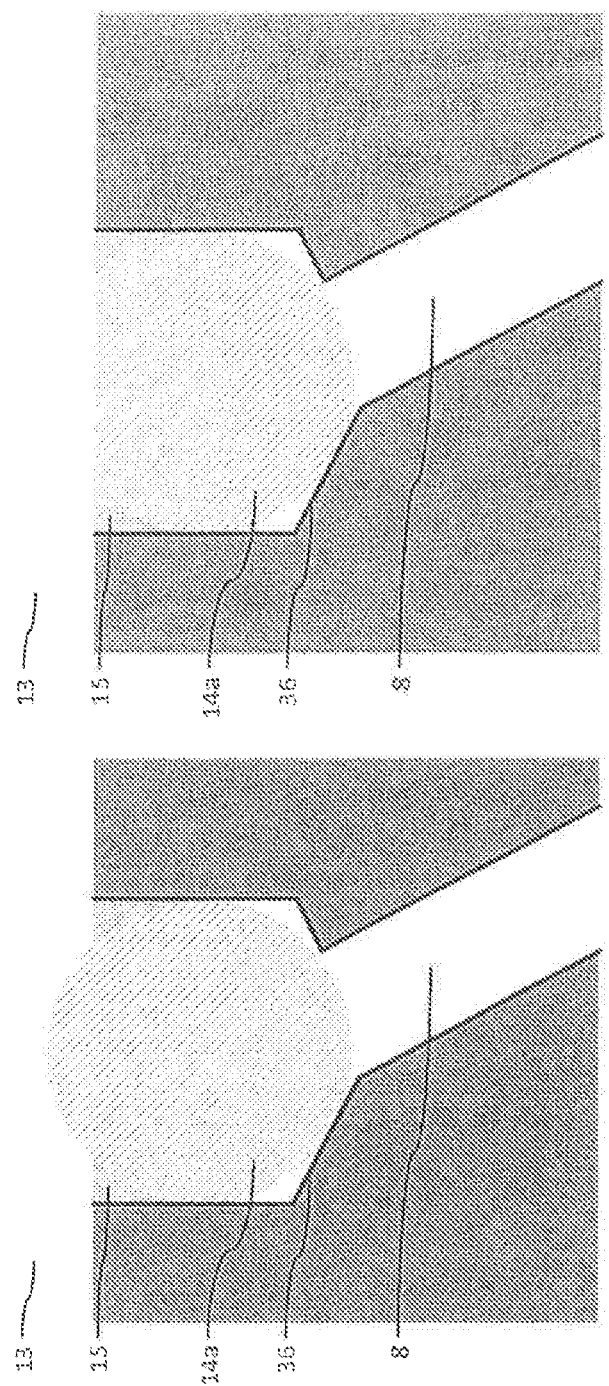

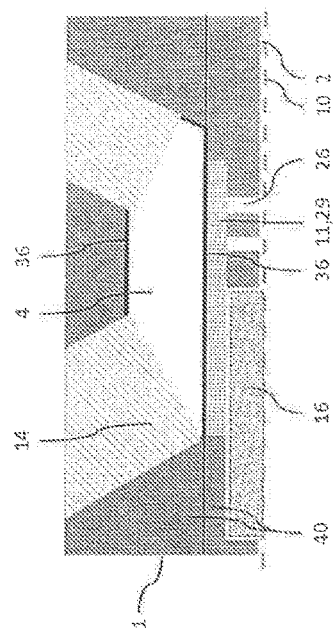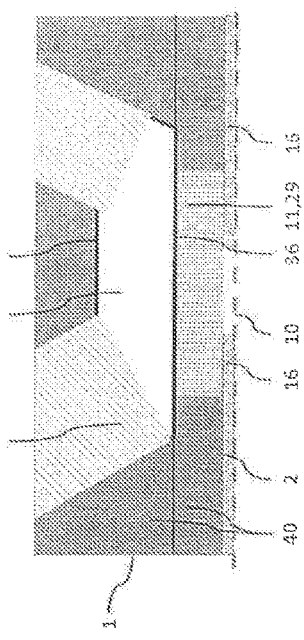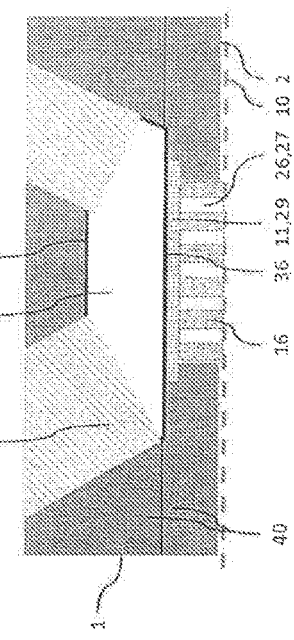

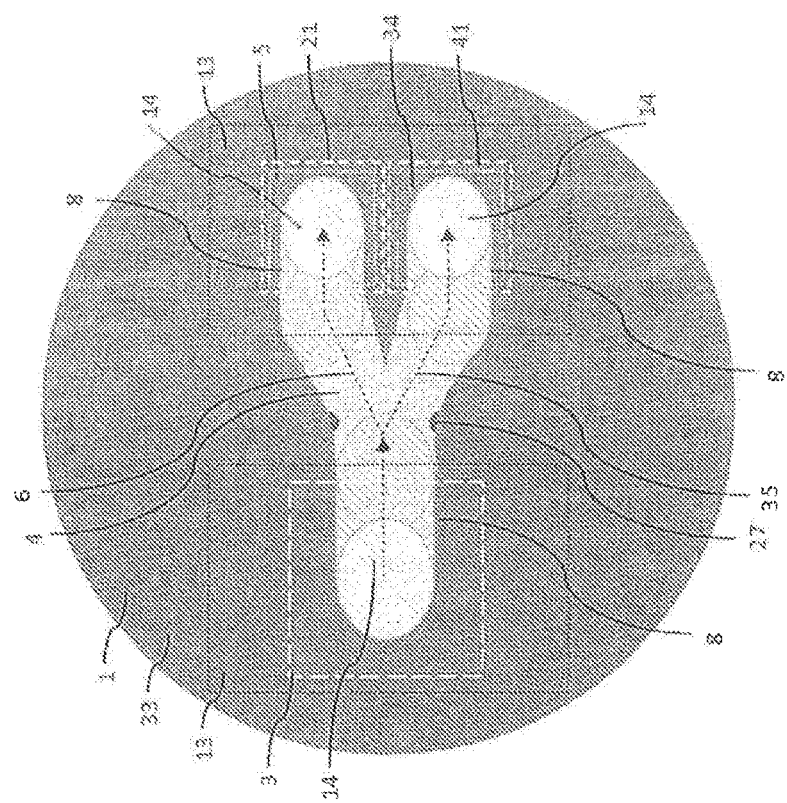

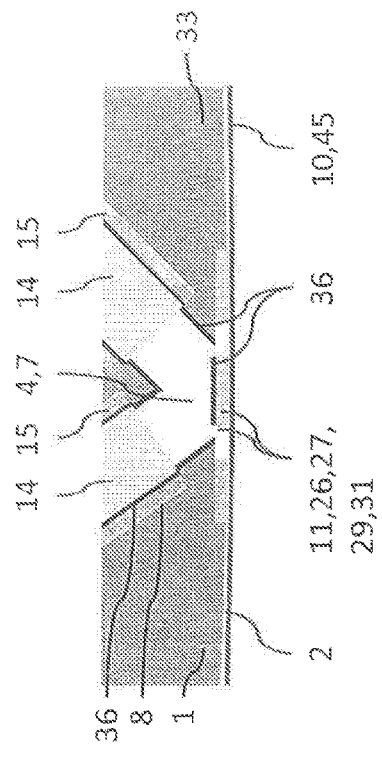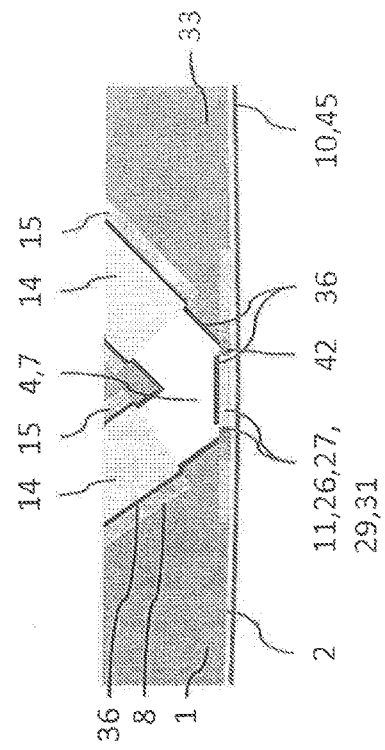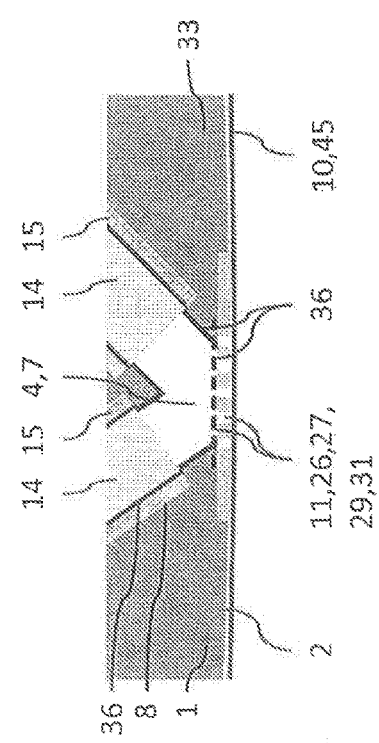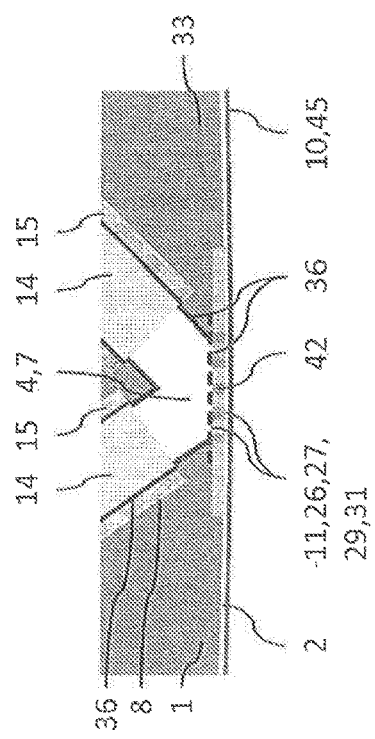

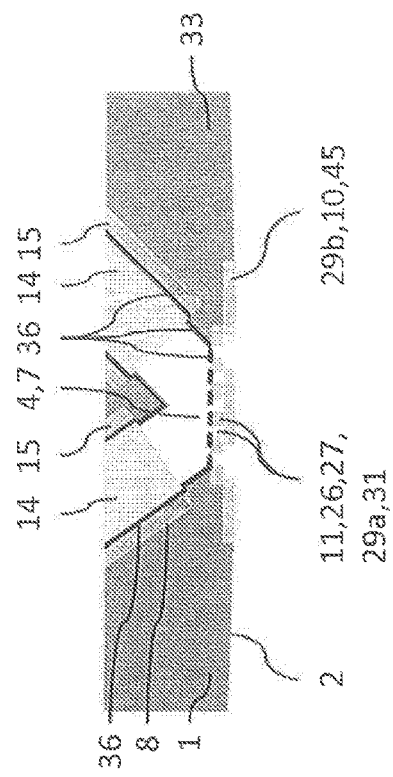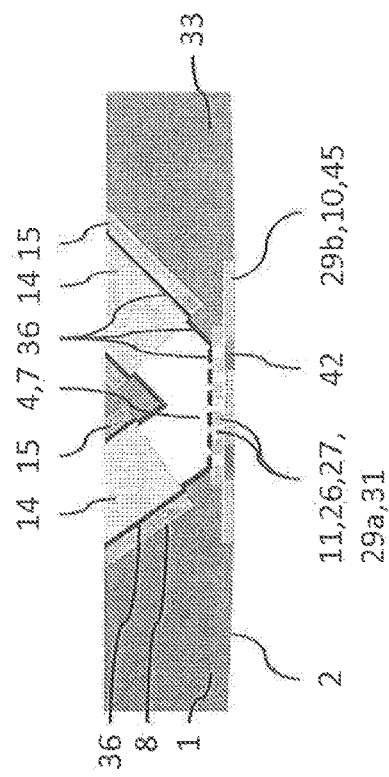

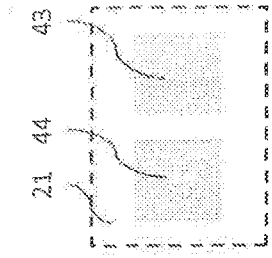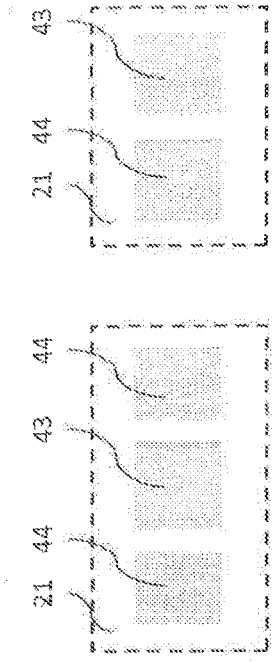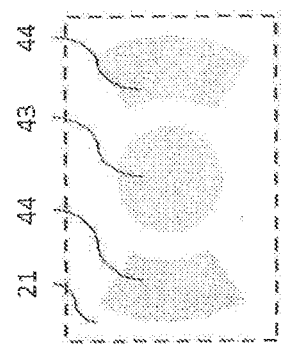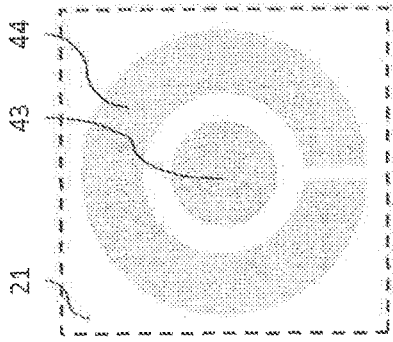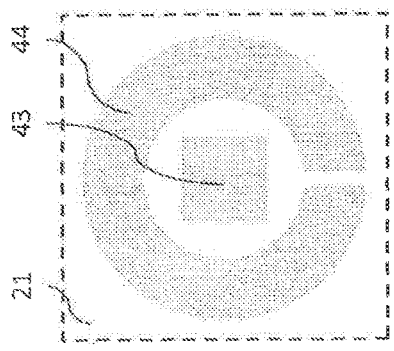

SENSOR FOR DETECTION OF GAS AND METHOD FOR DETECTION OF GAS

The invention is directed to a sensor for detection of gas and a method for detecting the occurrence or amount of gas.

Current systems for measuring gas employ a variety of measurement principles. In medical technology, predominantly electrochemical sensors are used for measurement of gases that have diffused transcutaneously, i.e. that have diffused through the skin of a human patient or of an animal. Current sensors for measurement of transcutaneous $CO_2$ are very sensitive and show good response times. Nevertheless, those sensors drift over longer measurement periods and require frequent calibrations, therefore, at the point of use, users need to use rather bulky calibration instruments including a calibration gas supply. Sensor calibration and maintenance impair the usability of the technology. Electrochemical sensors for measurement of transcutaneous gases are for example known from WO 2008/132205.

Today, measurement of transcutaneous blood gases, in particular of $CO_2$, is primarily used for continuous and noninvasive real-time monitoring of patient ventilation in virtually any clinical setting. Transcutaneous systems rely on the facts that gases diffuse through skin and body tissues and that the gases are detectable on the skin's surface by an appropriate sensor. The concentration of the detected gas is then typically translated into the arterial partial pressure of the gas using a mathematical relationship. This information provides a clear picture of the integrity and criticality of a patient's physical condition during treatment, in particular regarding aspects such as respiratory patterns, alveolar ventilation, pulmonary perfusion, or exclusion of $CO_2$ from ventilator and anesthesia circuits. Usually, the skin needs to be heated to 37° C.-45° C., preferably to 41° C.-43° C., to obtain clinically relevant measurement results.

Conventional noninvasive ventilation monitoring is performed by measurement of the concentration of respiratory gases in samples of a patient's breath. However, such technologies suffer from several drawbacks in certain clinical settings.

In certain clinical settings involving extracorporeal blood circulation, it is furthermore possible to measure blood gases directly from the blood stream of a patient.

One of the main technological challenges in transcutaneous gas sensing is related to the fact that the rates, at which the gases permeate through tissue and skin, are very low. Thus, a sensor for measurement of transcutaneous gases, whose measurement mechanism relies on equilibration of the concentrations of the gases in a measurement chamber with the respective concentrations in the skin, must have an extremely small volume of such a measurement chamber or the time to equilibration completion becomes unacceptably long. Moreover, an optical sensor employing such a measurement chamber has to overcome the challenge of guiding the optical radiation to, transmitting it through, and collecting it from the tiny measurement chamber while maintaining sufficient optical intensity. Another constraint is the measurement site which typically an earlobe of a grown-up patient or the thigh of a neonatal baby.

In U.S. Pat. No. 7,164,812 a sensor system is disclosed comprising a spiral optical waveguide through which an optical beam propagates from a light source to a detector. The evanescent field of the optical beam penetrates into the adjacent medium and can be absorbed by a chemical substance therein, e.g. by a transcutaneous gas.

Such a sensor system employs an optical fiber, which is difficult to integrate accurately into a small sensor. Furthermore, the short distance over which an evanescent field can interact with a substance requires high-precision manufacturing and assembly. Interferences of the evanescent field with numerous other substances than the gas to be measured can hamper the differentiation between wanted and unwanted signals.

In WO 2008/110927 a sensor system is disclosed comprising an optical sampling cell through which an optical beam propagates by single monomodal propagation from an emitter to a detector. The optical beam interacts with a gas within the sampling cell.

Such a sensor system is expensive, complex, and difficult to manufacture. Small deviations from the manufacturing specifications will dramatically affect the monomodal propagation and therewith system performance, thus tolerances need to be very tight. To maintain sensor reliability during use in the field is very hard to achieve and there is a risk of early failure.

It is an object of the present invention to avoid the drawbacks of the state of the art and in particular to provide a robust sensor for detection of gas, in particular for determining the concentration of small amounts of gas and a method for detection of gas, in particular determining the concentration of small amounts of gas which do not require frequent calibration and which deliver accurate results within acceptable response times.

Response time in this context is understood as the time a sensor requires from a certain condition, e.g. off patient, to reach 90% of a stable measurement value. Acceptable response times are shorter than 10 minutes, preferably shorter than 5 minutes and more preferably shorter than 2.5 minutes.

According to the invention this object is accomplished by a detector, a sensor and a method according to the independent patent claims.

According to a first aspect of the invention a detector for detection of electromagnetic radiation emitted by a source, typically for detecting measuring radiation in a sensor, is provided. Said detector comprises a first detection surface and a second detection surface and at least one wavelength sensitive element. The detection surface forms the area onto which radiation which should be detected impinges on the detector. The wavelength sensitive element is substantially transparent for radiation of wavelengths in a first wavelength band when this radiation is incident onto the wavelength sensitive element in a first range of incidence angles. Preferably exactly one common wavelength sensitive element is used for all of the detection surfaces. It is also substantially transparent for radiation of wavelengths in a second wavelength band when this radiation is incident onto the wavelength sensitive element in a second range of incidence angles. These first and second wavelength bands are at least partly different from each other, but may overlap. The first and second ranges of incidence angles are also at least partly different from each other, but may overlap. The wavelength sensitive element can furthermore be substantially transparent for radiation of wavelengths in further such wavelength bands and incident in further such ranges of incidence angles.

The wavelength sensitive element preferably is a wavelength filter such as an interference filter. A diffractive element is also conceivable. The filtering characteristics of wavelength filters based on interference layers are dependent on the angle of incidence of the impinging rays. Typically, the central wavelength of the passband of bandpass interference filters shifts to lower wavelengths when the angle of incidence increases; furthermore the passband shape may change. Therefore, a bandpass interference filter can be designed to possess a passband shape and central wavelength such that rays impinging at an angle of incidence (AOI) within a first range of incidence angles can only pass through the filter when their wavelength is within a first wavelength band, while rays impinging at an AOI within a second range of incidence angles can only pass through the filter when their wavelength is within a second wavelength band. While the wavelength bands and the ranges of incidence angles may but need not overlap, the second wavelength band typically extends to lower wavelengths than the first wavelength band when the second range of incidence angles extends to higher AOIs than the first range of incidence angles.

The first detection surface and the second detection surface and the at least one wavelength sensitive element are arranged such that radiation in the first wavelength band propagates through the wavelength sensitive element such that it impinges on said first detection surface and is detectable by said first detection surface. Correspondingly, radiation of the second or further wavelength bands propagates through the wavelength sensitive element such that it impinges on the second or further detection surfaces and is detectable by these second or further detection surfaces, respectively. Typically, when the radiation propagates through air before it impinges on the wavelength sensitive element, the incidence angles for the radiation having wavelengths within the first wavelength band may be from 0° to 30° with respect to the surface normal of the wavelength sensitive element and the incidence angles for the radiation having wavelengths within the second wavelength band may be from 25° to 60° with respect to the surface normal of the wavelength sensitive element.

Such a detector is suitable for miniaturization. Preferably, such a detector can be used in situations, where measuring radiation propagates as a beam consisting of non-parallel rays and particularly consisting of distinctly diverging rays and/or where beam shaping means such as collimators or concentrators cannot be used, for example due to size constraints. A beam consisting of distinctly diverging rays in this invention is understood as a beam undergoing an obvious change in cross-section when propagating through a short section of free space. This occurs for example when a beam contains significant amounts of rays forming angles exceeding 30°, and in particular exceeding 60°, to another significant amount of rays of the beam when propagating in air or vacuum. Furthermore, since only one wavelength sensitive element is applied in front of all detection surfaces, and not, as in a traditional approach, one wavelength sensitive element in front of each detection surface individually, the detection surfaces can be placed very close to each other and in principle can have arbitrary shapes, without constraints due to shape, size, and assembly of the individual wavelength sensitive elements. In particular, elimination of unwanted radiation passing from one wavelength sensitive element to an adjacent one is not an issue with only one wavelength sensitive element present. This allows the creation of detectors which are smaller and easier to assemble and which therewith also are cheaper.

Additionally and when the detection surfaces are not only sensitive to radiation but also to temperature, which typically is the case with many kinds of such detection surfaces, such a miniaturized detector is less prone to measurement errors arising from temperature differences since the detection surfaces can be placed close to each other and thus are more likely to be at the same temperature than when they are farther apart. This improves the measurement result, when the detector signals are temperature dependent.

Such a design enables the detection of radiation by a central detection surface and peripheral further detection surfaces. In particular, peripheral detection surfaces can be arranged concentrically with respect to the central detection surface. For example, a second detection surface can partly or substantially completely surround a first detection surface. Substantially surrounding in this context means that there might be small gaps between neighboring surfaces which allow the arrangement of conductors such as conductor paths. In particular, the second or any other peripheral detection surface substantially can be ring shaped.

A second detection surface surrounding a first central detection surface entirely or partly enables detection of more radiation of wavelengths in the second wavelength band, compared to when the second detection surface is located only at one side of the first detection surface. This leads to more exact measurement of the radiation in the second wavelength band, especially when a distinctly divergent radiation beam is to be detected which spreads to all sides of the central detector, for example a more or less rotationally symmetric beam forming a (solid) cone.

Gaps placed between individual detection surfaces can reduce an overlap between the corresponding ranges of incidence angles and hence between the corresponding wavelength bands of the detected radiation. Additionally, in such gaps and also in gaps between different parts of non-entirely surrounding detection surfaces, electrical contacts can be placed.

The detector can comprise exactly two detection surfaces.

Exactly two detection surfaces enable for example the detection of radiation in two corresponding wavelength bands when the detector is used e.g. for a gas sensor, where a lot of the radiation in the first wavelength band can be absorbed by the gas to be measured while radiation in the second wavelength band is rather or completely insensitive to the gas to be measured and hence can be used as reference radiation. For example, the radiation of this first wavelength band can be detected by a central detection surface and serves as signal radiation, while radiation in a second wavelength band at lower wavelengths is detected by a peripheral second detection surface and serves as reference radiation; alternatively signal radiation can also be detected by the peripheral detector while radiation in a second wavelength band at higher wavelengths is detected by a central detection surface and serves as reference radiation.

Alternatively the detector can also comprise exactly three detection surfaces. For example, it can be designed and placed such that the central and the outer peripheral detection surfaces primarily are sensitive to gas-insensitive radiation in wavelength bands substantially above and below the wavelength band of the radiation sensitive to the gas to be measured, respectively, while the primarily gas-sensitive radiation is detected by an inner peripheral detection surface. Such an arrangement simultaneously allows the detection of reference radiation below and above the range of gas-sensitive radiation and thus adaptation to spectral changes of the radiation emitted from the source.

The first and the second detection surfaces can be arranged on a common support, preferably a ceramic support, more preferably a support made of silica, in particular a form of quartz.

The use of a common support enables the creation of a miniaturized detector and helps to keep the detection surfaces at the same temperature.

According to another aspect of the invention, there is provided a sensor for detection of gas, in particular for detection of CO2, comprising a contact face which is directable towards a measuring site. The sensor comprises at least one radiation source, a measurement volume for receiving the gas to be measured, and a detector as previously described. The radiation emitted from the radiation source comprises at least two wavelengths, which are separable by the wavelength sensitive element of the detector. Said sensor comprises an optical gas-measuring path and a reference path. The detector is arranged such that radiation of the gas-measuring path impinges on one detection surface and radiation of the reference path impinges on the other detection surface.

Such a sensor can be built in a more compact way and with fewer parts and hence is simpler and easier to miniaturize.

Preferably the detector is arranged such that radiation in said first and said second wavelength bands are detectable by said first and second detection surfaces when measuring radiation is propagating within said sensor along a multitude of different optical paths from the radiation source through said measurement volume towards said detector and when the rays of said measuring radiation are distinctly divergent when they impinge on said wavelength sensitive element.

The detector can be arranged such that if measuring radiation rays of different wavelengths are propagating within a common beam towards the wavelength sensitive element the rays in different wavelength bands only propagate within separate beams from the wavelength sensitive element to said first and second detection surface. The wavelength sensitive element is then e.g. used to differentiate between radiation of measuring wavelengths and of reference wavelengths, which are individually propagating to their respective detection surfaces after entering the wavelength sensitive element.

According to still another aspect of the invention there is provided a sensor for detection of gas, in particular for detection of $CO_2$. The sensor uses an optical measurement principle: Infrared radiation is emitted by at least one radiation source and guided along at least one path through a measurement volume for receiving the gas to be measured onto at least a first radiation detector.

In context with this aspect of the invention one single detector having a first and a second detection surface and with one common wavelength sensitive element as described herein above can be preferably used.

Alternatively it is also possible to use a first and optionally one or more further detectors which are separate from each other. Optionally such detector(s) each may be provided with an individual wavelength sensitive element. Certain electronic properties of such a radiation detector depend on the intensity of the impinging radiation in such a way that by measuring them the intensity variations of the impinging radiation can be inferred employing an electronic circuit preferably comprising a microprocessor. Such a sensor furthermore comprises some diffusion paths connecting the sensor's contact face and its measurement volume.

When a sensor is mounted at the measurement site, molecules present in the vicinity of the contact face start diffusing through one or several membranes and possibly further diffusion paths into the measurement volume. The sensor is designed for molecule species that exist in gaseous form in the measurement volume. After some time, the molecule species to be measured in the measurement volume has equilibrated with the measurement site, i.e., the concentration of the molecule species in the measurement volume does not change any further as long as the concentration at the measurement site remains constant. After the equilibration period, the measured concentration is representative for the concentration at the measurement site and allows calculation of a desired parameter, for example arterial partial pressure of $CO_2$.

The wavelengths of the radiation emitted by the radiation source are chosen such that at least a part of the emitted radiation can be absorbed by the molecules that have diffused into the measurement volume and are present in the gas phase there. Measuring radiation according to the invention is radiation that can be detected by a first detector, for example radiation that can be absorbed by the molecule species to be measured or radiation that cannot be attenuated significantly by absorption by a gas and thus can serve as reference radiation. The more such gas molecules are present in the measurement volume, the more of the measuring radiation transmitted through the measurement volume is absorbed and the lower is the intensity of the measuring radiation impinging on a first detector sensitive for that radiation. In this way, the change of measuring radiation intensity impinging on a detector allows determining the concentration of a specific gas species.

The sensor comprises a contact face which is directable towards the measuring site of the gas to be measured. The sensor further comprises at least one radiation source, a measurement volume for receiving the gas to be measured and at least a first detector for detection of radiation transmitted from the source to the first detector through the measurement volume. The sensor comprises multiple paths of the radiation between radiation source and first detector. The radiation propagates along the paths in a non-imaging way.

At the measuring site, the molecules of the gas to be measured can be present in the gaseous phase or dissolved in a medium, for example dissolved in human tissue or in blood. For the measurement of transcutaneous gases, the measurement site is on the skin of a human or animal subject. For the measurement of respiratory gases, the measurement site is on some sort of channel, e.g. a tube, carrying exhaled breath.

To cause the radiation to propagate in a non-imaging way, not all optical elements along a path are imaging. Imaging optical elements present along the path do not have an imaging purpose. Consequently, radiation entering the measurement volume does not need to be characterized by a specific lateral and angular intensity distribution profile, as would be required for radiation propagating in an imaging system. In particular, the optical design of a sensor according to the invention aims for guiding and/or dividing the whole radiation beam emitted by the source, but does not attempt to influence individual rays of that beam, for example for the purposes of focusing or mutual alignment (collimation). Even in case elements are present within the device which can be used for influencing individual rays, they are not used for an imaging purpose. For example, such a non-imaging optical element can be a cylinder with reflective side walls, or a thick optical fiber, which solely has the purpose of guiding radiation from the entrance to the exit faces with minimal loss on the way.

Preferably, the intensity distribution profile at the entrance of the measurement volume is very uncharacteristic, i.e., no radiation path an emitted photon takes is preferred to another radiation path. As a result, any photon entering the measurement volume performs a random walk, characterized by numerous reflections. Consequently, also the intensity distributions at the exit of the measurement volume and at the detector surface are uncharacteristic. Along the path imaging optical elements can be present as long as they fulfill the above mentioned restrictions.

Any arbitrarily shaped reflectors or optical elements that do not attempt to form an image of a source may serve as non-imaging optical elements. This includes e.g. parabolic reflectors, compound parabolic concentrators, compound elliptical concentrators, optical cones, rough surfaces, etc.

Owing to the non-imaging and random-walk propagation of the radiation, the detailed geometrical shape of the optical elements confining and guiding the radiation is of much lower importance than for imaging systems. Hence, manufacturing tolerances can be significantly relaxed, which eases the production of the sensor. This is especially true for very small sensors and sensors having very small measurement volumes, such as sensors for measurement of transcutaneous gases. Furthermore, the production costs are lowered and the reliability of the sensor is enhanced.

The non-imaging optical elements can be an integral part of the sensor casing.

The term integral according to the invention is to be understood as part of the casing with a coating on the inside. No other separate non-imaging optical element need to be present in the channel.

Sensors comprising non-imaging optical elements as an integral part of the sensor casing are advantageous for miniaturization.

Non-imaging optical elements as integral part of the casing could for example be milled and drilled into a metal, preferably aluminum, or into plastics or molded. Surfaces of the non-imaging optical elements which are not sufficiently reflective can be coated with reflective layers.

Alternatively, it is furthermore possible to create a non-imaging optical element by filling a cavity, for example a hole or a channel, with a material that is transparent to the measuring radiation and may have a reflective layer on the outside. The non-imaging optical elements may be created in individual parts and combined later to the full optics or created within one part. The non-imaging optical elements can be embedded in a casing, e.g. a plastic casing. Thereby, individual non-imaging optical elements may be assembled to a combined optical element during the embedding procedure or they may be assembled beforehand and embedded as a whole optical element.

The path of the radiation can comprise at least one channel between the source and the measurement volume and/or between the measurement volume and the first detector, preferably the channel can comprise a filling.

The use of a channel enables the radiation being deflected by non-imaging optical elements to propagate from a source to the measurement volume and from the measurement volume to a detector. The use of a filling inside the channel improves the measurement results, since a filling can ensure that the gas content within the channel remains unchanged and hence the measurement cannot be biased by absorbing gas entering or leaving the channel.

Channel fillings preferably consist of materials substantially transparent to the measuring radiation, or of a combination of such transparent materials and further materials. Furthermore, filling materials can be present in channels primarily for the purpose of sealing, i.e., for preventing gas exchange between the channel and its vicinity.

A channel preferably has reflective surfaces or surfaces with reflective coatings, unless the channel comprises a transparent filling that is reflectively coated on all surfaces except the radiation entrance and exit surfaces. This leads to less optical absorption of measuring radiation and hence to an improved measurement signal.

A channel can be cylindrical. A cylindrical channel can be drilled into a material or formed by injection molding or comprise a tube. This enables cost-effective manufacturing. Furthermore, cylindrical channels are easier to fill completely with transparent materials. Preferably, a filling for a cylindrical channel is of cylindrical or at least partially spherical shape.

Generally other forms of channels are conceivable.

Typical channel diameters are substantially 0.3 to 2 mm or preferred substantially from 0.5 to 0.8 mm. Lengths of the channel can be substantially between 2 and 5 mm.

The measurement volume can have reflective surfaces with reflectances exceeding 90%, preferably exceeding 95%, and more preferably exceeding 98%.

Those surfaces are highly reflective for radiation of wavelengths in the range of interest for the gas concentration measurements.

The measurement volume furthermore comprises surfaces where radiation is supposed to enter or exit. Such transmissive surfaces are characterized by low reflectances below 35%, preferably below 15%, and more preferably below 7%.

The measurement volume may comprise yet further surfaces exhibiting lower reflectances than the high-reflection surfaces. Such lower-reflection surfaces are undesired and their surface area is sought to be minimized, but often they cannot be avoided completely. Examples for lower-reflection surfaces are seals around channel fillings, openings of diffusion paths connecting measurement volume and contact face such as gas-access holes or pores, or inner membranes preventing the measurement volume from contamination.

The measurement volume may have inherent and non-degrading high-reflection surfaces, obtained when forming the measurement volume by milling or drilling into a well-reflecting material such as a metal like Al (aluminum), Ag (silver), Cu (copper), Mo (molybdenum), W (tungsten), or Au (gold). Alternatively, at least a part of the measurement volume can be formed in or from materials that are not highly reflective or whose reflectances are expected to degrade with time, such as plastics, certain metals or metallic alloys or most other materials. In particular, injection molding of plastics is a cheap and therefore attractive manufacturing method. Such materials need to be coated at some stage with a reflective coating such as Al, Au, TiN (titanium nitride), Cu, Ag, Mo, or W, and/or a protective coating such as PTFE (Polytetrafluoroethylene), Parylene, $Al_2O_3$ (aluminum oxide), $Si_xN_y$(silicon nitride), $MgF_2$ (magnesium fluoride) etc., which creates and/or preserves the required high-reflection surfaces. Furthermore, lower-reflection surfaces can at least partially be converted to high-reflection surfaces by similar coatings with reflective and/or protective materials.

Alternatively, the measurement volume can be formed by joining two plates or plate-like elements, of which at least one is shaped such that after joining a cavity is created at the interface of the two plates.

The measurement volume can be arbitrarily shaped. However, its volume must be small in order to be suitable for transcutaneous gas sensing; preferably its volume is less than 10 $mm^3$, more preferably less than 2 $mm^3$, and even more preferably less than 1 $mm^3$. Additionally, the measurement volume fits into a cuboid of 5 mm×5 mm×3 mm in size, but it does not fill that cuboid volume by far. Preferably, the measurement volume fits into a cuboid of 2 mm×2 mm×1 mm in size, or into a cuboid of 1.5 mm×1.5 mm×1 mm in size.

The minimum aperture of the measurement volume, i.e. the minimum cross-sectional area of the measurement volume between the radiation entrance and exit openings, is at least 0.15 mm$^2$ and preferably at least 0.3 mm$^2$.

The measurement volume comprises a wall or section of a wall, where diffusion paths end in the measurement volume, i.e., where the molecules to be measured can enter the measurement volume. The wall can be non-porous, e.g. consist of an inner membrane where the gas molecules to be measured can diffuse through. The wall can also be porous, i.e., contain a number of irregularly or regularly or deliberately arranged openings or pores or holes. For example, the openings can consist of drilled or ablated holes, of etched pores, or of random paths through porous material. Preferably, most or the entire surface of the wall directed to the measurement volume is intrinsically reflective for the measurement radiation or contains a reflective and/or protective coating.

According to another aspect of the invention there is provided a sensor for detection of gas, in particular for detection of $CO_2$, comprising a contact face which is directable towards a measuring site of the gas to be measured. The sensor has a receiving interface adapted for receiving an outer membrane in a receiving position, at least one radiation source, a measurement volume for receiving the gas to be measured and at least a first detector for detection of the transmitted radiation. The radiation is transmitted through the measuring volume. The sensor comprises an inner membrane between measurement volume and the receiving position for protecting the measurement volume.

Preferably, the sensor further comprises the features of a sensor as described previously.

The receiving position determines the position of a membrane which is either part of the sensor or part of a carrying object for the membrane. In one embodiment, the outer membrane is simply covering the contact face completely, during use.

The inner membrane hence may be arranged inside the sensor or even covering the contact face, especially in case an outer membrane is not part of the sensor itself.

In case the inner membrane does not have contact to the outside of the sensor the demands on mechanical robustness as well as on chemical resistance of the inner membrane are minimized. This is due to the membrane being protected from direct impact from the outside. Especially in case the inner membrane forms a boundary of the measurement volume, the inner membrane preferably is reflective for the measuring radiation or contains a reflective coating.

The use of an inner membrane enables the use of a second outer membrane integrated into a disposable device as for example an applicator such as a patient applicator as described in WO 2013/064313, which is used for applying the sensor on a measurement site. The measurement volume will not be polluted by particles or fluids even when the outer membrane is not part of the sensor. Additionally, the use of an inner membrane enhances the protection of the gas cell in any case.

The inner membrane can be a non-porous membrane, preferably a membrane made of a polymer, more preferably a membrane made of a fluoropolymer such as PTFE (Polytetrafluoroethylene) or a polyethylene (PE) or a polypropylene (PP).

Other possible materials are PFA (Perfluoroalkoxy), PCTFE (Polychlorotrifluoroethylene), PVDF (Polyvinylidene fluoride), FEP (Fluorinated ethylene propylene), polyester, polyethylene terephthalate (PET), polyethylene (PE), nylon, polymethylpentene, Parylene, polyethersulfone (PES), polysulfone (PS), acrylic copolymers, cellophane, rubber, or a silicone elastomer such as silastic, etc. As polyethylenes possible materials can comprise UHMWPE (ultra-high-molecular-weight polyethylene), HDPE (High density polyethylene), LDPE (low-density polyethylene), etc.

Such a membrane is gas-permeable but fluid-impermeable and hence protects the measurement volume.

The inner membrane can alternatively be a porous, fluid-impermeable membrane in particular a membrane comprising a porous polymer or ceramic or semiconductor or metal, such as ePTFE, nanoporous aluminum oxide, porous silicon, or sintered or etched films or thin sheets.

The use of a porous membrane improves gas permeability while the membrane nevertheless remains fluid-impermeable.

A porous inner membrane preferably consists of polymeric membranes comprising ePTFE (expanded PTFE), PTFE, PES, PS, PVDF, PP, (nano-)fibers, nylon, acrylic copolymers, or membranes comprising glass fibers or sintered or pressed metallic or ceramic powders, or membranes comprising porous ceramics or semiconductors such as nanoporous aluminum oxide, porous titania, porous silicon, a zeolite, porous glass, silicon dioxide, silica gel, a clay, or membranes comprising a polymer, ceramic, or metal with pores deliberately introduced through chemical or track etching, ablation, erosion, drilling, or other treatment, in particular alumina, silica, silicon, titanium, titania, silicon nitride, PTFE, aluminum, stainless steel, polycarbonate, or polyester.

The inner membrane can be a reflective membrane, in particular reflective to radiation to be detected by the first detector.

A reflective surface of the inner membrane or a reflective coating on the surface of the inner membrane is an important advantage since it can hinder radiation in the measurement volume from getting absorbed by the inner membrane or from getting lost through the pores. The size of the pores influences the reflectance.

The inner membrane can comprise hydrophobic and optionally also oleophobic pores, in particular pores with openings smaller than 5 µm and preferably with openings smaller than 1 µm with a reflective top coating and a hydrophobic pore coating.

The pores may be inherent to the material. Alternatively, the pores or pore-like structures may have been randomly or deliberately caused by stretching, chemical or electrochemical or track etching, ablation, drilling, erosion, etc. of a suitable precursor material. Furthermore, the inner membrane can comprise a combination of different porosities such as fine pored and coarse pored or porous and free of pores. The inner membrane may furthermore have been created by pressing or sintering powders or particles of a suitable material.

Preferably, the pores or pore-like structures have hydrophobic and optionally also oleophobic surface properties or can be modified, e.g. by coating, such that the pore surfaces attain these properties.

This hinders liquids from entering the measurement volume.

The inner membrane can comprise a gas collection mechanism.

This improves the gas collection efficiency of the sensor and therefore decreases the response time of the sensor.

The gas collection mechanism can comprise specific channels or pores to collect the gas from a measuring site. Also deliberately structured or scratched surfaces or surfaces with a controlled surface roughness in the range of 100 μm to 1 μm can be used as a gas collection mechanism.

In case the inner membrane comprises the gas collection mechanism, no separate gas collection mechanism needs to be integrated, which reduces the complexity of sensor assembly.

At least during use the contact face can comprise an outer membrane.

An outer membrane protects the sensor and in particular the measurement volume from contaminating substances such as dirt, application or sealing gel, sweat, cleaning fluids, or other liquids or particles. In case the outer membrane gets damaged, for example during cleaning or disinfection, it can be replaced by a new outer membrane. When the sensor also comprises an inner membrane, the measurement volume remains protected even when the outer membrane is not attached to the sensor, for example during membrane change.

The outer membrane can be fluid-impermeable and gas-permeable, in particular comprising a fluoropolymer such as PTFE or a polyethylene or a polypropylene or a porous polymer or ceramic or semiconductor or metal, such as ePTFE, nanoporous aluminum oxide, porous silicon, or sintered or etched films or thin sheets.

Such an outer membrane is mechanically and chemically robust and nevertheless thin.

The outer membrane can essentially consist of the same materials as could be used for a porous or non-porous inner membrane described above.

According to another aspect of the invention there is provided a sensor for detection of gas, in particular for detection of $CO_2$, which comprises a contact face which is directable towards the measuring site of the gas to be measured. The sensor further comprises at least one radiation source, a measurement volume for receiving the gas to be measured and at least a first detector for detection of the transmitted radiation, wherein the radiation is transmitted through the measurement volume. The radiation source and at least the first detector are arranged in a compartment. The compartment is separated from the measurement volume by at least one sealing element.

Advantageously, this sensor is combined with features of a sensor as described previously.

The compartment can comprise separate areas for at least one radiation source and at least one detector which are separated by a radiation-impermeable and/or a thermally isolating element. Hence, the term compartment does not necessarily imply one single open room for the electronic parts of the sensor.

A sealing element in a channel between a source and the measurement volume or in a channel between the measurement volume and a detector inhibits gas molecules from diffusing from the measurement volume into the channel or vice versa, or from the compartment into the channel or vice versa.

Alternatively, the source can simultaneously be used as a sealing element. For example, the source can be a filament lamp having a bulb which is arranged as a sealing element in the channel. Such an embodiment leads to high radiation intensity in the measurement volume. Furthermore, the number of parts of the sensor is reduced since a separate sealing element is not needed anymore.

Sealing elements seal a channel between measurement volume and channel or between compartment and channel. This ensures that no gas capable of absorbing measuring radiation can be exchanged between measurement volume and channel or between compartment and channel, since the measurement would be biased by a changing concentration of such gas in the measurement volume or in the compartment. Thus, sealing elements improve the measurement accuracy.

The sensor can comprise at least one channel between radiation source and detector, wherein the at least one sealing element can be arranged near an end of the channel and is at least partially tapered, such that the cross-section of the tapered part becomes smaller towards the center of the channel.

Preferably, the tapered part of the sealing element has circular cross-sections.

Such a partially tapered sealing element can be pressed into the channel and lead to a hermetic seal. In particular, it leads to a large sealing surface between sealing element and channel wall.

The non-tapered parts of the partially tapered sealing element can basically have any shape. Preferably the non-tapered parts have elliptical, circular or hexagonal shapes.

The sealing element can also be at least partially spherical or elliptical. Preferably, the sealing element can be a sphere.

Such an at least partially spherical sealing element can be pressed into the channel and lead to a hermetic seal. Furthermore, in particular spherical sealing elements are available as standard high-precision parts on the market and hence do not need to be custom produced, which leads to lower production costs.

In addition, the use of the at least partially spherical shapes can be beneficial for the optical throughput, since the amount of total internal reflection can be reduced. This leads to improved measurement accuracy.

The sealing element can also be cylindrical. Preferably the sealing element can be an elliptical or circular cylinder.

Cylindrical in the sense of the application is to be understood as a mathematical definition of cylindrical, hence comprising different base areas such as circles, ellipses, rectangles or hexagons.

A cylindrical sealing element can lead to the elimination of gases inside the channel and hence enhance the measurement accuracy. A cylindrical sealing element can be a combination of a sealing element and a filling in one element.

A channel between the radiation source and the measurement volume can be sealed by two sealing elements, preferably by two sealing spheres, wherein one sealing element is facing the radiation source and the second sealing element is facing the measurement volume.

The use of two or more sealing elements leads to a simple design of the sensor and nevertheless to an accurate measurement result. The sealing elements are easily introduced into the channel and lead to hermetically sealed channels. With two or more sealing elements, also non-cylindrical or furcating channels, such as Y-shaped channels, can be sealed.

A channel between the first detector and the measurement volume can be sealed by two sealing elements, preferably by two sealing spheres, wherein one sealing element is facing the first detector and a second sealing element is facing the measurement volume.

The use of two or more sealing elements leads to a simple design of the sensor and nevertheless to an accurate measurement result. The sealing elements are easily introduced into the channel and lead to hermetically sealed channels. With two or more sealing elements, also non-cylindrical or furcating channels, such as Y-shaped channels, can be sealed.

Preferably, all channels are sealed by sealing elements.

Preferably, a channel that is sealed by more than one sealing element is sealed by sealing elements near every end of that channel.

This leads to a larger volume of the channel being gas-free.

Measuring radiation needs to propagate through a channel in order to get from a source via measurement volume to a detector. Therefore, the sealing element can be made of a material substantially transparent to the radiation to be detected by the first detector. Preferably, the sealing element is made of sapphire, ruby, silicon, aluminum oxynitride, or an infrared-transparent glass such as a fluoride glass or quartz.

This leads to a higher radiation intensity impinging onto the detector and hence to a more accurate measurement result.

The sealing element can further be made of yttria, YAG, spinel or a polymer. As a fluoride glass e.g. ZBLAN can be used. The sealing element can be manufactured by machining, casting, molding, or sintering such materials or their precursors, or by a combination of these methods. Casting, molding, or sintering are preferable methods for creating sealing elements especially in non-cylindrical and furcating channels, such as Y-shaped channels.

Since the radiation propagates through the sealing elements, a sealing element comprises an entrance surface, through which the radiation enters the sealing element, and an exit surface, through which radiation exits the sealing element. The entrance and in particular the exit surfaces can be polished, non-polished or deliberately scratched.

Furthermore, the sealing element can be at least partially coated with a reflective layer. It is advantageous to coat the sealing element with a reflective layer, except on the entrance and exit surfaces, especially if only one sealing element extending from near one end of a channel to near every other end of that channel is used. Alternatively or additionally, a reflective layer can be deposited onto the inner surfaces of the channel.

A reflective coating on the sealing element prevents radiation within the sealing element from leaving the same and from getting absorbed by materials in or on or of the channel that are less transparent than the sealing element and that do not have a very good reflectance. This leads to a higher radiation intensity impinging onto the first detector and hence to a better measurement result.

The sensor may comprise a seal between sealing element and channel, preferably a seal created from a polymer such as epoxy.

In case the sealing properties of a sealing element are not guaranteed to be sufficient for preventing gas exchange between channel and its vicinity, an additional seal between sealing element and channel can be used. Preferably, the seal is made of a material which can flow during or after application and which becomes or can be turned solid afterwards. This ensures that the seal can fill any voids between sealing element and channel and then remains there to fulfill its sealing function. Preferably, a seal comprises a polymer prepared by curing a liquid resin, such as epoxy, or comprises a metal prepared by casting or soldering, or comprises sintered or pressed ceramics or glass like LTCC or glass frit. Seals can also be made of elastic materials pressed in between the sealing element and the channel. For example, a seal can be created by an O-ring or a silicone elastomer around a sealing element.

If measuring radiation can propagate through a seal, it is advantageous if the seal is very transparent for the measuring radiation or else if it is thin, such that it does not absorb measuring radiation.

According to another aspect of the invention there is provided a sensor for detection of gas, in particular for detection of $CO_2$, comprising a contact face which is directable towards a measuring site of the gas to be measured. The sensor comprises at least one radiation source, a measurement volume for receiving the gas to be measured and at least a first detector for detection of the transmitted radiation. The radiation is transmitted through the measurement volume. The sensor comprises a water trap arranged such that water molecules are at least partially removed from the measurement volume.

Advantageously, the sensor is combined with features of the sensors as described previously.

A water trap according to the invention is everything that can capture water from the vicinity of the water trap, in particular everything that can capture water molecules from a gas mixture.

Liquid water inside the measurement volume can absorb vast parts of the optical signal, which is undesired. The use of a water trap can keep a gas mixture, in particular the gas mixtures in the measurement volume and diffusion paths, sufficiently dry such that no condensation of water occurs. This keeps the quality of the measurement signal sufficiently high.

The water trap can be a desiccant, in particular a molecular sieve, a silica gel, or a zeolite.

Other possible materials are activated charcoal, calcium sulfate, calcium chloride, clay, or soda lime. Preferably, the water trap does trap water molecules but not molecules of the gas to be measured. Most preferably, the water trap is a 3A molecular sieve.

A desiccant is a standard component and can easily and cost-efficiently be integrated into a sensor.

The water trap is integrated into the sensor such that it is in contact with a gas mixture that can access the measurement volume. One or several water traps can be used within one sensor. The water trap can be integrated into the measurement volume wall, especially if it does not absorb significant amounts of measuring radiation. If the reflectivity of the water trap is insufficient, the water trap can be coated by a reflective coating.

The water trap can also be arranged near or around diffusion paths, such that water molecules moving between contact face and measurement volume can be trapped by the water trap.

The water trap can also be integrated into other parts of the sensor such that molecules from the gas mixture in the measurement volume can reach the water trap via an exchange channel.

Furthermore, the sensor can comprise an exchange channel from the water trap to the environment, or the water trap can directly be in contact with the environment. Since the sensor typically is heated, the relative humidity in the environment usually is lower than in the measurement volume and therefore the water trap can give off some water to the environment. Therewith, the water trap is prevented from becoming saturated. This reduces the demands on the trapping capacity of the water trap. Hence, the water trap can be smaller and the sensor lifetime longer.

The water trap can furthermore be separated from the measurement volume by an exchange channel, in which a water-permeable object is arranged, preferably close to the measurement volume. The water-permeable object is at least slightly permeable for $H_2O$ molecules, while the water-permeable object's permeability for the gas species to be measured, e.g. to $CO_2$, is reduced or the water-permeable object is further impermeable for the gas species to be measured. Preferably the water-permeable object comprises an ionomer such as Nafion.

The advantage of placing such a water-permeable object in an exchange channel is that it confines the gas to be measured to a smaller volume, since the gas cannot access the exchange channel behind the water-permeable object at a relevant permeation rate. This allows keeping the sensor's response time short.

It is furthermore possible to create an exchange channel leading to the environment, in which a water-permeable object is arranged but in which no water trap is present, such that water molecules from the gas mixture in the measurement volume can reach the environment. Preferably, a reflecting element is placed in front of or at the entrance of the exchange channel. In this case, the environment acts as a water trap.

The sensor can comprise an exchange channel from the water trap to an environment.

The relative humidity of the environment will always be lower than the relative humidity in the measurement volume. Hence, the water trap can give off some water to the environment and thus the water trap can never be saturated. This leads to a longer lifetime of the water trap in the sensor.

The water trap can further be arranged in a disposable part of the sensor, such as in a patient applicator. If the water trap is arranged in a disposable part, it can be easily exchanged before it is saturated. Preferably, the water trap is arranged in a disposable applicator such as a patient applicator, where the water trap is automatically replaced with every new sensor application. This ensures the water trap remains functional and sensor performance reliable.

The sensor can further comprise a reflecting element, which is permeable, for gases and at least for water molecules and which is arranged in the exchange channel or covering the exchange channel. Preferably the reflecting element is a membrane comprising a porous polymer or ceramic or semiconductor or metal, such as ePTFE, nanoporous aluminum oxide, porous silicon, or sintered or etched films or thin sheets, preferably coated with a reflective coating.

For example, the reflecting element can be arranged close to the measurement volume or as a part of a measurement volume wall. The reflecting element preferably reflects measuring radiation Such a reflecting element can prevent measuring radiation from being absorbed and from getting lost through the exchange channel. Preferably, a reflecting element is arranged at the entrance or in front of an exchange channel, in which a water trap and a water-permeable object or just a water trap are arranged.

The reflecting element can also fulfill functions of an inner membrane. Preferably, the water trap is then arranged such that it resides between the reflecting element and the contact face, at least during use. Preferably, such a water trap is a part of a disposable applicator or patient applicator.

According to another aspect of the invention, there is provided a sensor for detection of gas, in particular for detection of $CO_2$. The sensor comprises a contact face which is directable towards the measuring side of the gas to be measured. The sensor further comprises at least one radiation source, a measurement volume for receiving the gas to be measured and at least a first detector for detection of the transmitted radiation, wherein the radiation is transmitted through the measurement volume. The sensor further comprises a wavelength filter to filter the radiation detected by the first detector. Furthermore, a numerical aperture converter (NA converter) is arranged in a path between the wavelength filter and the radiation source. In particular, the NA converter can be arranged between the wavelength filter and the measurement volume, preferably adjacent to the wavelength filter.

An NA converter according to the invention deflects a significant amount of rays of the measuring radiation, which would otherwise impinge on the wavelength filter at an incidence angle exceeding a certain threshold angle, such that they impinge on the wavelength filter at a lower incidence angle. Hence, such an NA converter does not create a beam of parallel or nearly-parallel rays, as a collimator would. It only confines the angular spread of the rays to some extent, typically to within 20°-30° half angle. The NA converter achieves such a confinement by conversion of high-angle rays exceeding a certain threshold angle to lower-angle rays, e.g. by deflection at appropriately angled mirror surfaces. NA converters in practice may also have a range of threshold angles and limited efficiency, but still are characterized in that they convert a significant portion of high-angle rays to lower-angle rays.

Preferably, this sensor is combined with features of gas sensors as previously described.

Wavelength filters are transparent for radiation of certain wavelengths and opaque for further radiation. Usually, wavelength filters are designed to be transparent for radiation of a certain wavelength band, the nominal pass band, where the radiation impinges at normal incidence. Pass-band position and shape are dependent on the angle of incidence of the radiation. Thus, radiation of wavelengths outside the nominal pass band may pass through the filter when the angle of incidence is high enough. Such radiation usually is undesired radiation. In addition, useful radiation of wavelengths within the pass band may be rejected by the filter when the angle of incidence is high enough. Such radiation is lost radiation.

The use of an NA converter reduces the amount of radiation impinging onto the wavelength filter at high angles of incidence, which leads to a better filtering capability of the wavelength filter. Thus, less undesired radiation of wavelengths outside the nominal pass band and more useful radiation of wavelengths within the nominal pass band can pass the wavelength filter. This enhances the significance of the detected signal with respect to the concentration of the gas to measure, which ultimately leads to a more accurate measurement result.

Preferably, the NA converter is created as an opening in a reflective or opaque material with the shape of a parabolic reflector, a compound parabolic concentrator, a compound parabolic concentrator, a compound elliptical concentrator, an optical cone, or any other geometrical object that is at least partially tapered. NA converters can be produced for example by milling, drilling, or injection molding. Furthermore, an NA converter needs to have reflective surfaces. Thus the NA converter can be formed of a material having inherently high reflectance or its surfaces can be coated with a reflective material.

The height of the NA converter can be substantially 0.3 to 2.5 mm or preferred 0.5 to 1.5 mm. Minimum openings of the NA converter can be of any shape and substantially 0.07 to 2.3 $mm^2$ in area or preferred round or rectangular and substantially 0.15 to 0.80 $mm^2$ in area. Maximum openings of the NA converter can be of any shape and substantially 0.15 to 9 mm² in area or preferred round or rectangular and 0.25 to 2.3 mm² in area.

Alternatively, a NA filter can be used.

An NA filter corresponds to an NA converter, except that the NA filter confines the angular spread of the rays by absorption of high-angle rays instead of by conversion.

Furthermore, an NA converter can comprise a transparent filling. The transparent filling is transparent for measuring radiation and can be formed such that it partially or completely fits into the NA converter. A transparent filling eliminates gas partially or completely from the NA converter and thus reduces the risk of absorption of measuring radiation by gas present in varying concentrations within the NA converter, which would bias the measurement result. Transparent fillings can be created by machining transparent materials such as sapphire, ruby, yttria, YAG (Yttrium aluminum garnet), spinel, aluminum oxynitride, or silicon, or an infrared-transparent glass such as a fluoride glass, e.g. ZBLAN, or a polymer, or by casting, molding, or sintering such materials or their precursors.

Furthermore, an NA converter can also be produced by creating a transparent part having the shape of a transparent filling completely filling the void of an NA converter. The transparent part requires a reflective coating, except on the radiation entrance and exit faces. Such an NA converter corresponds to an NA converter perfectly filled by a transparent filling and is easier to integrate into the sensor.

According to another aspect of the invention there is provided a sensor for detection of gas, in particular for detection of $CO_2$. The sensor comprises a contact face which is directable towards a measuring site of the gas to be measured. The contact face comprises a gas collector having a collection area from which the gas is collected. The sensor further comprises at least one radiation source, and a measurement volume for receiving the gas to be measured, wherein the measurement volume comprises an access area directed to the contact face and being permeable for the gas. The sensor further comprises at least a first detector for detection of the transmitted radiation, wherein the radiation is transmitted through the measurement volume. The collection area of the gas collector is larger than the access area of the measurement volume.

The access area is defined as the area on the measurement site from where gas can diffuse into (or out of) the measurement volume during use when no gas collector is present. The collection area is defined as the area on the measurement site from where gas can diffuse into the measurement volume during use when a gas collector is present.

Preferably, this sensor is combined with features of sensors as previously described.

By having a collection area larger than the access area, the collection of gas from the measurement site, in particular from the skin, is more efficient, since gas molecules from a larger area of the measurement site are able to diffuse into the sensor. This leads to a faster equilibration of the gas concentrations in the measurement volume with the corresponding molecular concentrations at the measurement site, in particular with the concentrations in the skin. This in turn decreases the sensor response time. Alternatively or additionally, including a gas collector allows to increase the size of a measurement volume without compromising response time, which leads to a higher radiation throughput through the measurement volume and ultimately to increased sensor accuracy.

The total gas-accessible volume of the gas collector has to be small since it adds to the overall volume the diffusing gas needs to access. Preferably, the accumulated volume of the diffusion paths is less than fifty times the volume of the measurement volume, more preferably smaller than five times the volume of the measurement volume, and even more preferably smaller than one time the volume of the measurement volume.

The gas collector can basically have any shape. Preferably, the gas collector spreads over an area such that the collection area substantially is smaller than 350 mm², preferably smaller than 180 mm² and greater than 5 mm².

The gas collector can comprise diffusion paths for the gas, wherein the diffusion paths comprise contact pores and collecting channels and wherein the diffusion paths lead from the contact face to the measurement volume or to further diffusion paths leading to the measurement volume.

The diffusion paths, in particular collecting channels, may be open towards the contact face or buried or a combination of open and buried.

The diffusion paths can be formed between deliberately structured or scratched surfaces or two surfaces with a predefined surface roughness, in particular in the range of 100 μm to 1 μm.

At least one of these surfaces can be an inner or outer membrane.

Such a design allows efficient cross diffusion between measurement volume and contact face of the sensor.

This leads to short response times of the sensor.

According to another aspect of the invention there is provided a sensor for detection of gas, in particular for detection of $CO_2$, comprising a contact face which is directable towards a measuring site of the gas to be measured. The sensor comprises at least one radiation source and a measurement volume for receiving the gas to be measured. The measurement volume comprises a permeable wall directed towards the measuring site and at least a first detector for detection of the transmitted radiation. The radiation is transmitted through the measurement volume. The permeable wall comprises a porous surface, which reflects radiation, wherein pore openings of the porous surface preferably have dimensions smaller than 5 μm. More preferably the pore openings have dimensions smaller than 1 μm.

Preferably, the sensor is combined with features of sensors as previously described.

The use of a porous surface which reflects radiation keeps radiation inside the measurement volume but nevertheless allows gas molecules to enter the measurement volume.

Since the overall volume accessible to the gas to be measured needs to be kept small, such a permeable wall can be thin and small to lead to acceptable response times of the sensor.

The permeable wall can serve as an inner membrane as previously described.

The permeable wall can essentially comprise the same materials as could be used for a porous inner membrane, in particular nanoporous aluminum oxide, or porous silicon, or sintered or etched films or thin sheets coated with a reflective layer. Preferably, the reflective layer is made from Al, Au, TiN, Cu, Ag, Mo, or W. The reflective layer needs to be applied such that it does not clog the pores and hence allows gas to enter the measurement volume.

Any one of the previously described sensors can comprise a radiation source emitting radiation in a relatively broad range, typically in the infrared range and having an emission bandwidth of a few micrometers. Typically and preferably a thermal radiator may be used as a radiation source.

The thermal radiator is operated at temperatures where measuring radiation is emitted at sufficient intensity, typically above 400° C. Often, thermal radiators have emission spectra approaching a black body emission spectrum. In particular, thermal radiators emit radiation in a wavelength band significantly broader than the absorption band of the gas to be measured.

The use of an efficient thermal radiator leads to accurate measurement results for reasonable driving power.

Alternatively the radiation source can comprise an infrared LED.

The use of an infrared LED may be advantageous, since it loses less thermal energy to the sensor than a thermal radiator and since it can be pulsed at high frequencies. This can lead to a favorable signal-to-noise ratio of a detector signal and therewith to accurate measurement results. Furthermore, if the emission band of the LED is sufficiently narrow, wavelength filters may be omitted for at least the first detector. However, also LEDs emitting radiation in a wavelength band broader than the absorption band of the gas to be measured may be used.

Furthermore, the radiation source can comprise an infrared laser, such as a VCSEL, emitting sufficient measuring radiation.

The use of an infrared laser is advantageous, since it typically emits very narrow-band radiation at very high intensity and can be pulsed at high frequencies. This can lead to a favorable signal-to-noise ratio of a detector signal and therewith to accurate measurement results. Furthermore, wavelength filters may be omitted for at least the first detector.

A sensor casing can be gas tight. The sensor casing at least comprises measurement volume, diffusion paths, channels, radiation source, and detector. Of course gases accessing or leaving the measurement volume through diffusion paths and gases accessing or leaving the measurement volume or diffusion paths through deliberately introduced exchange channels are permitted in a gas-tight sensor casing.

A gas-tight sensor casing leads to accurate measurement results, since no gas capable of absorbing measuring radiation in the radiation paths and hence of biasing the measurement result can be exchanged with the environment, except in the measurement volume.

Radiation at least in a range between 1 and 12 µm, preferably in a range between 1 and 5 µm, and more preferably in a range between 3 and 5 µm or between 2 and 4 µm can be detectable by the first detector.

The wavelength band between 1 and 12 µm and in particular between 1 and 5 µm contains absorption lines of gas to be measured, especially of $CO_2$.

The measurement volume can have a volume smaller than 10 $mm^3$, preferably smaller than 2 $mm^3$, and most preferably smaller or equal to 1 $mm^3$.

The concentrations of the gas species contained in such a measurement volume can be equilibrated with the corresponding concentrations at a measurement site on the skin of a patient within acceptable response times and furthermore such a measurement volume allows the optical radiation to propagate through the measurement volume.

The sensor can comprise an individual second detector or a single detector with a first and a second detection surface and a second path between the measurement volume and the second detector as described herein above.

The use of a second detector or second detection surface allows simultaneous measurements of different gas species contained in the measurement volume.

It also allows a comparison of the intensities of the radiation impinging on the two detectors or detection surfaces, where radiation falling onto the first detector can be absorbed by the gas to be measured and radiation falling onto the second detector cannot be absorbed by the gas to be detected. This allows detecting a change in the radiation intensity emitted by the radiation source, which for example may happen over time due to aging of the source. Such a detected change can be used to correct the measurement results, which enhances the accuracy of the sensor, especially the long-term accuracy.

The second path can be at least partially separated from a path between first detector and measurement volume.

The separation of the paths enables the radiation to reach a second detector. Preferably, the separation of the paths occurs close to the detectors, such that the measurement surroundings are to a large extent identical for radiation impinging on the two detectors.

For example, the main separation of the paths can be also designed to occur within a wavelength sensitive element. Alternatively, path separation can be achieved in a sealing element, preferably a sealing element between measurement volume and detector compartment, or in the measurement volume, or alternatively in the source compartment.

Alternatively, the separation of the paths can also be obtained by use of a beam splitting NA converter. The beam splitting NA converter can be arranged at the end of a channel filling close to the first and second detector. The beam splitting NA converter is on the one hand a reflector which divides the radiation beam emerging from the channel filling into two separate beams and on the other hand simultaneously converts rays impinging at angles exceeding certain threshold angles to lower angles (like an NA converter). Such a design enables using two detectors with only one channel, preferably a channel with a filling, which enables the design of a smaller and faster sensor that is in addition less sensitive to condensation and corrosion due to the late separation of the radiation beams. A beam splitting NA converter can consist of two conical angled holes, for example with elliptical cross-section, in a plate, where the smaller hole openings overlap and are facing the sealing element while the larger hole openings still overlap or are spatially separated and are facing the detectors.

There is further provided a method for detection of gas, in particular of $CO_2$, preferably using a sensor according to the previous description. Radiation is emitted from at least one radiation source, transmitted through a measurement volume and detected by a detector. The gas to be measured is received in the measurement volume after having diffused transcutaneously into the measurement volume. The radiation propagates in a non-imaging way between radiation source and detector.

The propagation in a non-imaging way enables the creation of a miniaturized sensor which is able to detect gas diffusing transcutaneously from skin with acceptable response times. Manufacturing tolerances can be significantly relaxed, which eases the production of the sensor. This is especially true for very small sensors and sensors having very small measurement volumes, as it is required for measurement of transcutaneous gases. Furthermore, the production costs are lowered and the reliability of the sensor is enhanced.

Liquids, such as cleaning fluids or sweat, or viscous liquids, such as gels, can be prevented from entering the measurement volume.

The presence of liquids or viscous liquids can lead to false measurement results, due to the radiation absorption characteristics of liquids. Means for preventing liquids or viscous liquids from entering the measurement volume are membranes, which are not permeable for liquids.

Water vapor can be at least partially removed from the gas mixture containing the gas to be detected, in particular, from the gas mixture contained in the measurement volume and in the diffusion paths.

The removal of water vapor reduces relative humidity and thereby reduces the possibility of water condensation in the measurement volume or in the diffusion paths.

The radiation can be at least partially transmitted through an NA converter and a wavelength filter.

The use of an NA converter and a wavelength filter reduces the amount of radiation with wavelengths outside the filter's nominal pass band and increases the amount of radiation with wavelengths within that nominal pass band, compared to using a wavelength filter without NA converter.

This leads to a more accurate measurement result.

According to another aspect of the invention there is provided a method for detection of gas, in particular of $CO_2$, preferably as described above. In particular the method is conducted using a sensor according to the previous description. Radiation is emitted from at least one radiation source, transmitted through a measurement volume and detected by a detector. The gas to be measured is received in the measurement volume after having diffused transcutaneously into the measurement volume. The gas is collected by a gas collector having a collection area which is larger than the access area of the measurement volume.

By having a collection area larger than the access area, the collection of gas from the measurement site, in particular from the skin, is more efficient, since gas molecules from a larger area of the measurement site are able to diffuse into the sensor. This leads to a faster equilibration of the gas concentrations in the measurement volume with the corresponding molecular concentrations at the measurement site, in particular with the concentrations in the skin, which decreases the sensor response time. Alternatively, including a gas collector can allow to increase the size of a measurement volume without compromising response time, which leads to a higher radiation throughput through the measurement volume and ultimately to increased sensor accuracy.

It is further possible to combine different measurement methods in one sensor such as measurements of temperature, multi-wavelength pulse oximetry, transcutaneous oxygen (tcPO2), further radiation intensities for self-calibration purposes, or further gas concentration measurements.

Such a combination in one sensor can be advantageous in application.

The sensor as described above can further comprise a temperature control device. The temperature control device can comprise a heater and a temperature sensor.

The temperature control device preferably keeps the temperature of the sensor in a range of 37 to 50° C. and preferably in a range of 41 to 45° C.

Additionally, the sensor is connectable to a power unit. It is also connectable to or contains a signal processing unit which controls sensor operation and which may amplify, convert, and process the signals measured by a detector. The powering and the signal processing units can be integrated into one electronic device or into separate electronic devices, or a unit can be split into separate partial units and such full or partial units can be integrated into separate electronic devices.

When such separate electronic devices are placed some distance away from the sensor head, small sensor heads can be designed which are particularly suitable for application on skin.

Additionally, the sensor as described above can comprise a changing mechanism comprising at least two wavelength filters to change the active wavelength filter used for filtering the measuring radiation. The changing mechanism may be integrated in the form of a wheel, bow, or array.

The possibility of changing the wavelength filter enables the detection of different absorption lines and hence of different gases in one sensor. Furthermore, it enables to perform self-calibration measurements, which leads to a more accurate measurement result.

A sensor according to the invention having a porous inner and/or outer membrane can comprise a pore filling made from a gas-permeable material, in particular a polymer such as a silicone (e.g. polydimethylsiloxane, etc.) or a fluoropolymer (e.g. polytetrafluoroethylene, an amorphous fluoropolymer, etc.).

Such a pore filling inhibits contamination and clogging of the pores and prevents condensation of water in the pores.

It is further an option that only one of the membranes of the sensor comprises a pore filling. In particular, the outer membrane can comprise a pore filling. The outer membrane could for example consist of a metal, for example steel, titanium, aluminum, etc., or of a ceramic compound, such as aluminum oxide, silicon nitride, etc., or of a glass, comprising a polymeric pore filling.

Such a design would lead to an optimal combination of diffusion of gas into the measurement volume and obviation of contamination and water condensation.

It is further conceivable that a third membrane is present during application, which is part of a patient applicator for example as described in WO 2013/064313. In this case, three membranes are present in total during application, and the outer membrane attached to the sensor becomes an intermediate membrane.

A sensor (without communication and power supply) according to the invention preferably fits into a virtual cylinder having a diameter of 30 mm and a height of 20 mm or into a virtual volume of 15 $cm^3$. More preferably, the sensor fits into a cylinder having a diameter of 20 mm and a height of 16 mm or into a virtual volume of 5 $cm^3$. Most preferably, the sensor fits into a cylinder having a diameter of 17 mm and a height of 13 mm or into a virtual volume of 3 $cm^3$.

Within such a sensor fitting into such volumes the complete measuring optics of the sensor is arranged, but communication and power supply means such as electrical cables are excluded. All measuring radiation rays propagating along optical paths from emitter to detector are confined to this volume. In particular, no optical fibers guiding measuring radiation into or from the sensor are connected to the sensor.

Furthermore, the sensor preferably only communicates with other devices such as PCB or display by electric or electronic means. In this case there is no optical communication with the sensor from outside.

Preferably the total length of the shortest complete optical path from the source via the measurement volume to a detector or a detection surface, i.e. of the shortest path followed by measuring radiation, does not exceed 20 mm and preferably does not exceed 10 mm. Such a design allows the creation of a miniaturized sensor which is e.g. favorable in context with medical sensors such as $CO_2$ sensors.

The shortest complete optical path from the source via the measurement volume to a detector or a detection surface, i.e. the shortest path followed by measuring radiation, leads through gas-inaccessible volumes like channel fillings and through gas-accessible volumes like the measurement volume or unfilled space between a channel filling and a source.

It is further preferred that the sum of the lengths of those sections of this shortest complete optical path leading through gas-accessible volumes other than the measurement volume does not exceed 3 mm, preferably does not exceed 1.5 mm, and more preferably does not exceed 0.8 mm. Such a design improves the measurement result: If gas to be measured diffuses into such gas-accessible volumes other than the measurement volume with time, it biases the measurement result, which deteriorates measurement accuracy. When the typical optical path lengths through gas-accessible volumes other than the measurement volume are designed to be short and, in particular, to be shorter than the typical path length through the measurement volume, the influence of that bias is reduced and the measurement result remains more accurate. Furthermore, such a design also enables the introduction of venting openings leading from such gas-accessible volumes other than the measurement volume to the environment without introducing a significant bias owing to measuring gas present in the environment.

Preferably, the average electrical power delivered to the sensor during typical measurement conditions, which excludes an initial warm-up phase, is below 5 W, more preferably below 2 W and most preferably below 1 W.

Exceeding these power values can lead to increased sensor temperatures that might lead to skin burns in case the sensor is applied to a patient's skin.

The invention is further explained with reference to preferred embodiments and the following drawings which show:

FIG. 1 A schematic cross-sectional view of a sensor, illustrating how radiation propagates from a source via the measurement volume to a radiation detector, and possible arrangements enabling gas access to the measurement volume.

Figure 2:
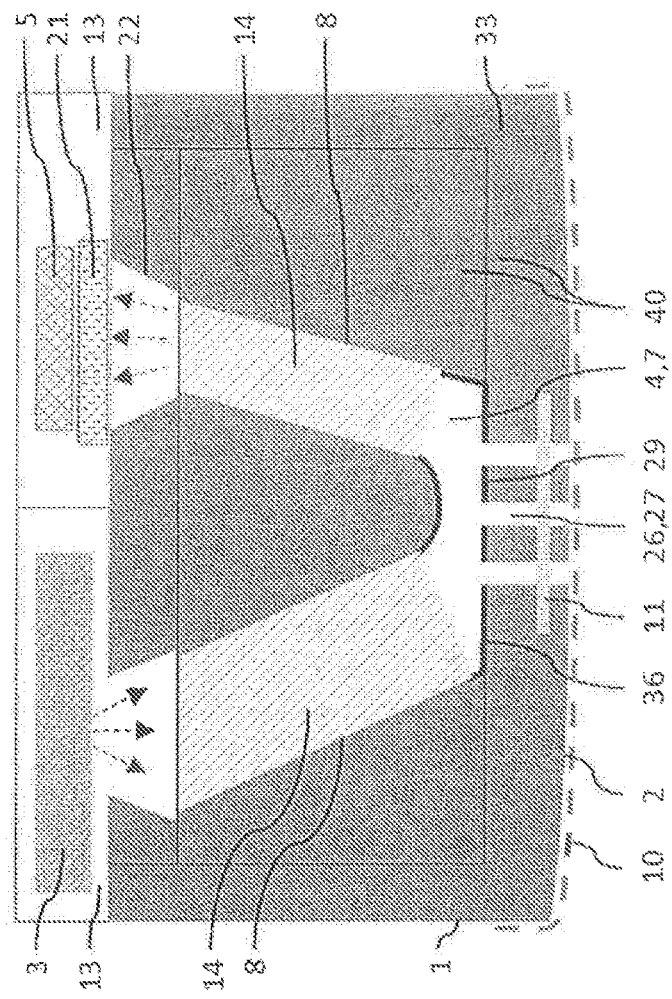

FIG. 2 A schematic cross-sectional view of a sensor, illustrating a possible shape of a non-imaging measurement volume and possible arrangements enabling gas access to the measurement volume.

Figure 3:
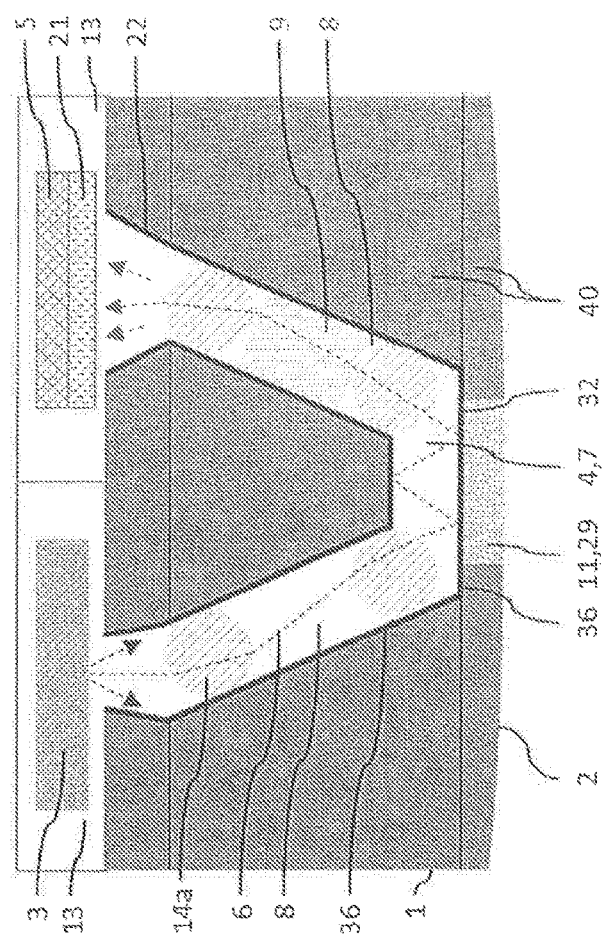

FIG. 3 A schematic cross-sectional view of a sensor, illustrating how radiation propagates from a source via spherical sealing elements into the measurement volume and from there through further spherical sealing elements, an NA converter, and a wavelength filter to a radiation detector.

Figure 4:
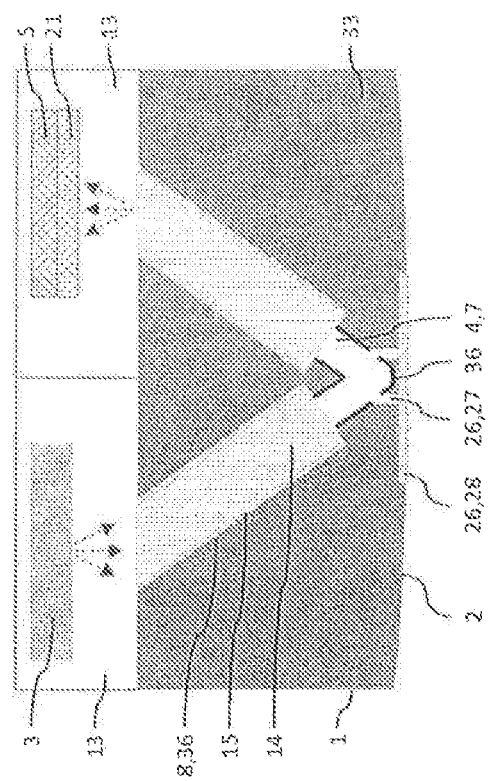

FIG. 4 A schematic cross-sectional view of a sensor, illustrating a further shape of a non-imaging measurement volume and a further way of filling a channel.

FIG. 5 A schematic cross-sectional view of a sensor detail, illustrating a reflective permeable wall of the measurement volume FIG. 6 A schematic cross-sectional view of a sensor detail, illustrating an inner membrane comprising a gas-collection mechanism.

FIG. 7a,b Two schematic cross-sectional views of a sensor detail, illustrating how an at least partially spherical sealing element and a seal may be arranged to seal a channel.

Figure 8B:
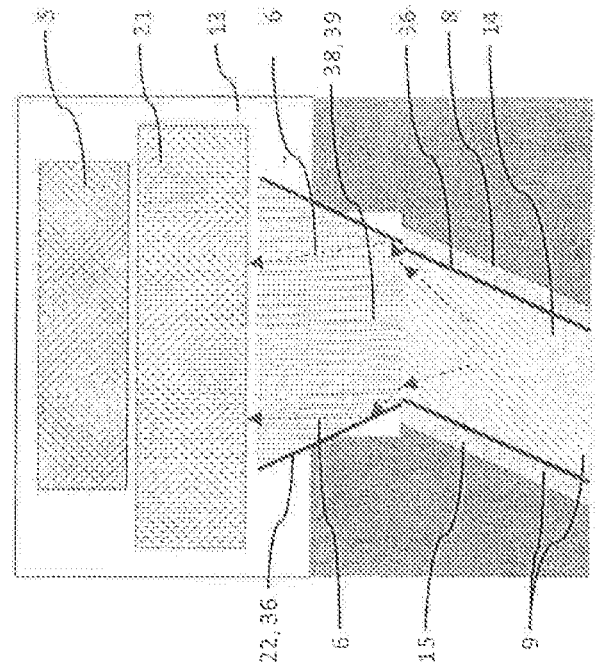
Figure 8A:
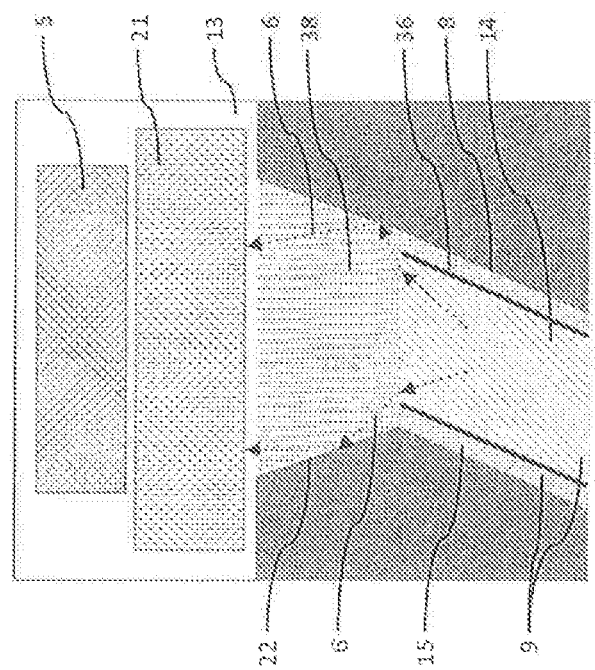

FIG. 8a,b Two schematic cross-sectional views of a sensor detail, illustrating how rays leaving a sealing element at high angles are converted by an NA converter to rays with low incidence angles before impinging onto a wavelength filter.

Figure 9:
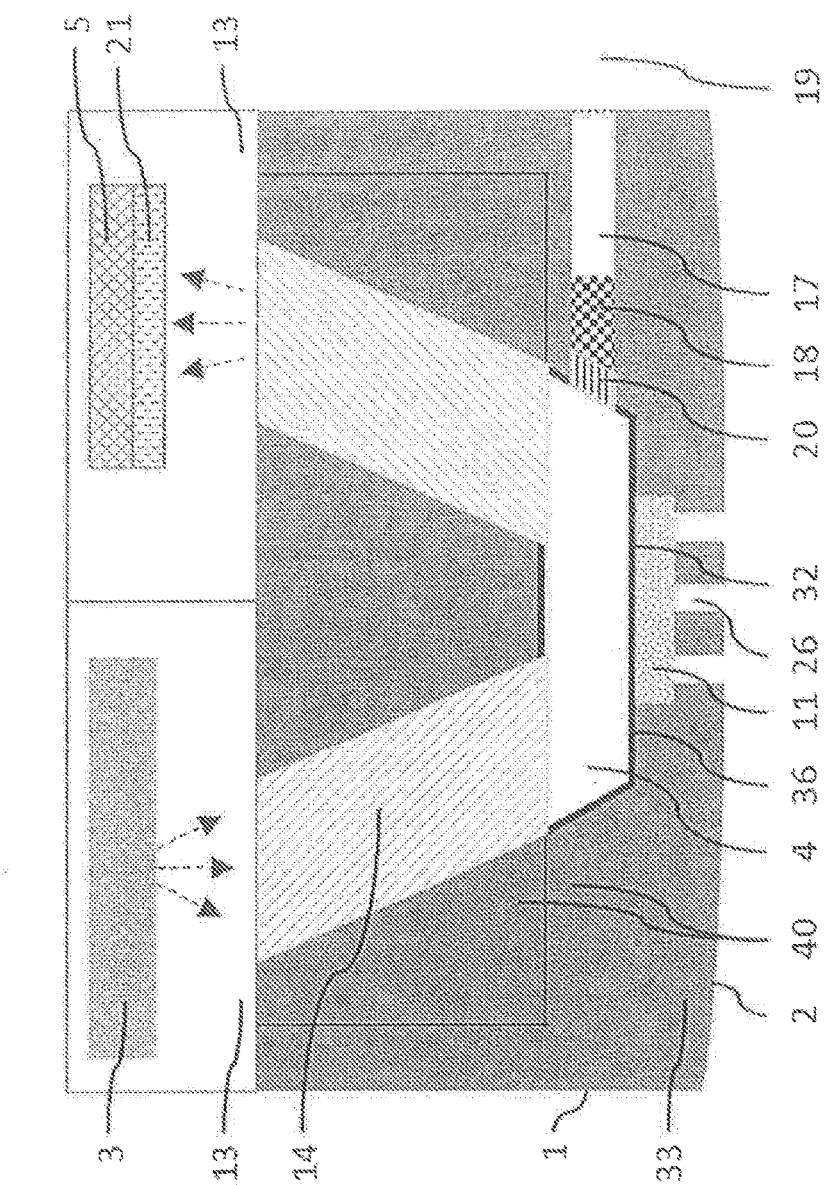

FIG. 9 A schematic cross-sectional view of a sensor, illustrating an exchange channel leading to an environment.

Figure 10:
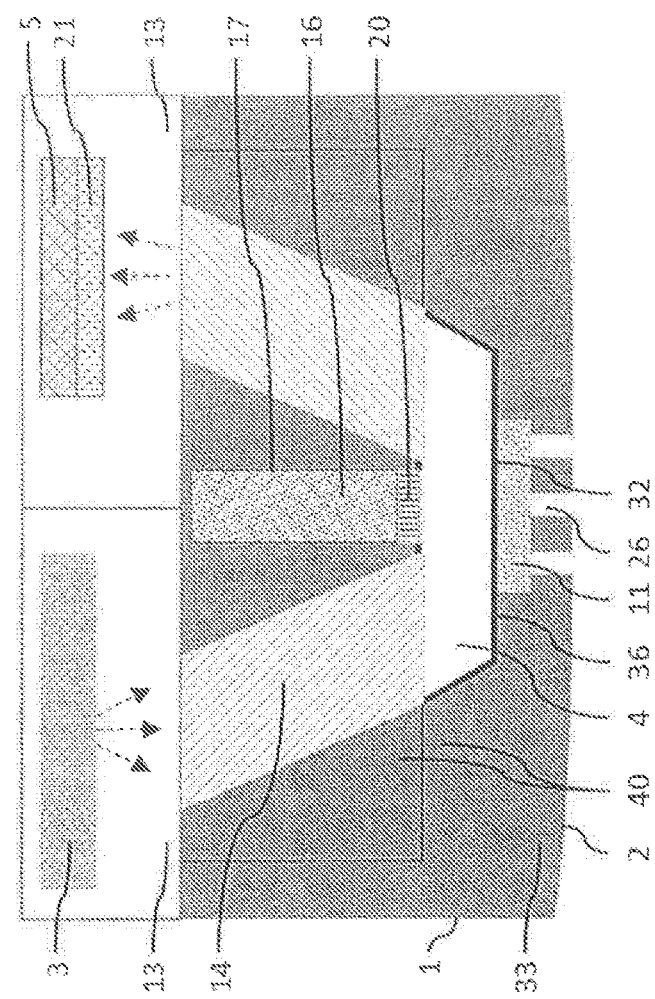

FIG. 10 A schematic cross-sectional view of a sensor, illustrating an exchange channel comprising a desiccant.

FIG. 11a,b,c Schematic cross-sectional views of sensor details, illustrating three arrangements of water traps in a disposable part of the sensor.

Figure 12A:
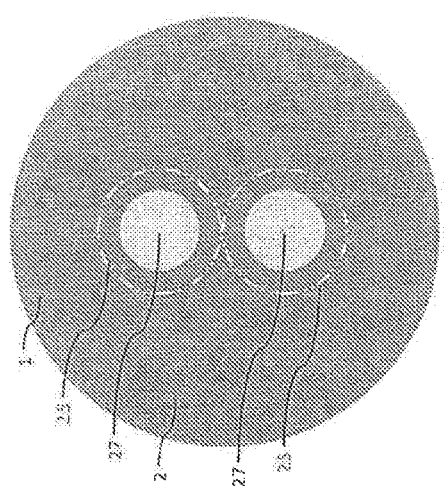

FIG. 12a,b Schematic views onto a detail of the contact face of a sensor, illustrating the access and collection areas in the absence and presence of a gas collector.

FIG. 13 A schematic top-down view of a sensor, illustrating how radiation propagates along a second path from a source onto a second detector.

Figure 14B:
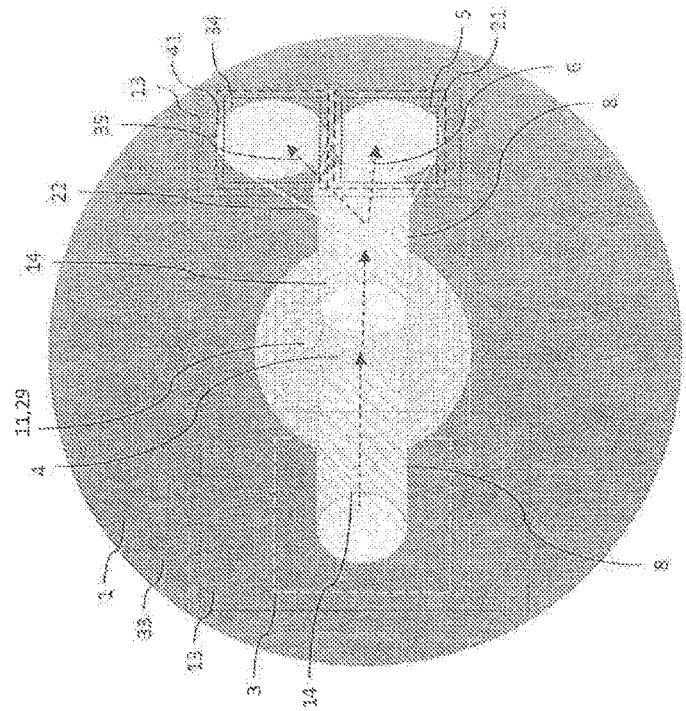
Figure 14A:
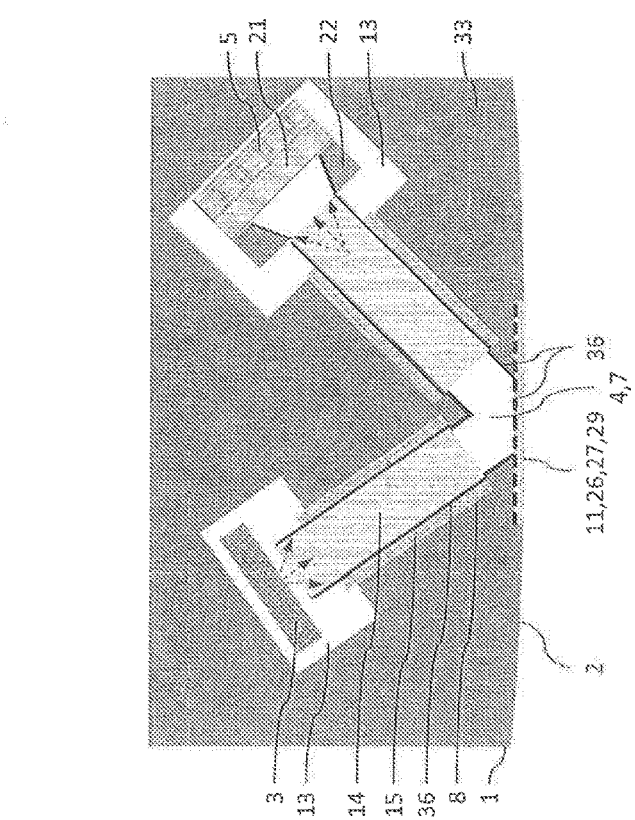

FIG. 14a,b Schematic cross-sectional and top-down views of a further sensor embodiment with a beam splitting NA converter.

Figure 15A:
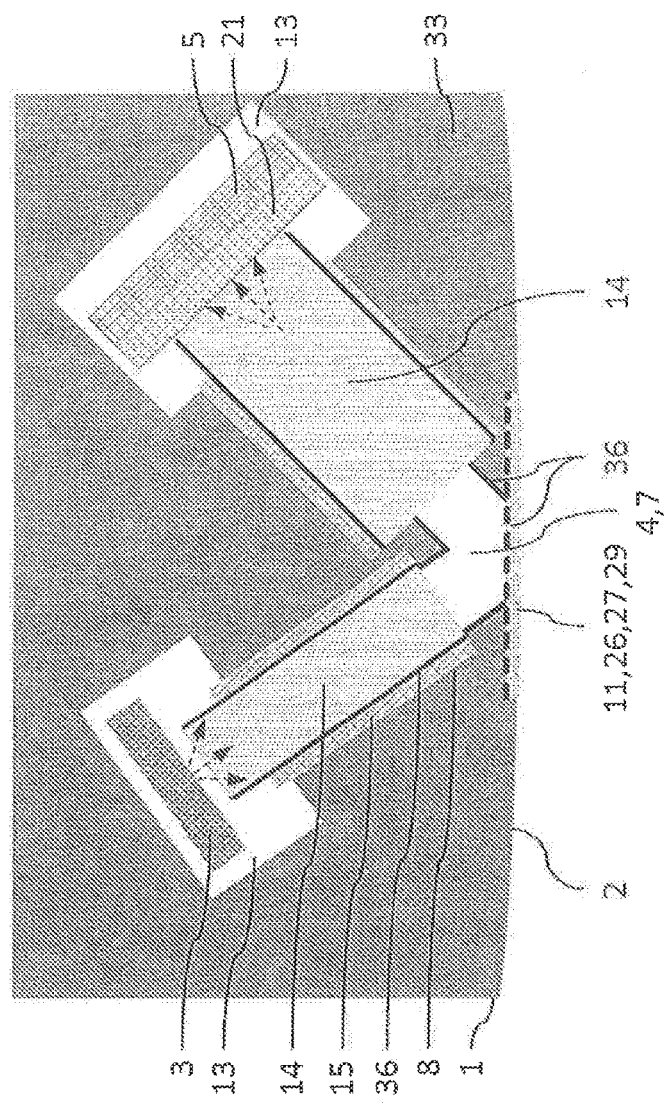
Figure 15C:
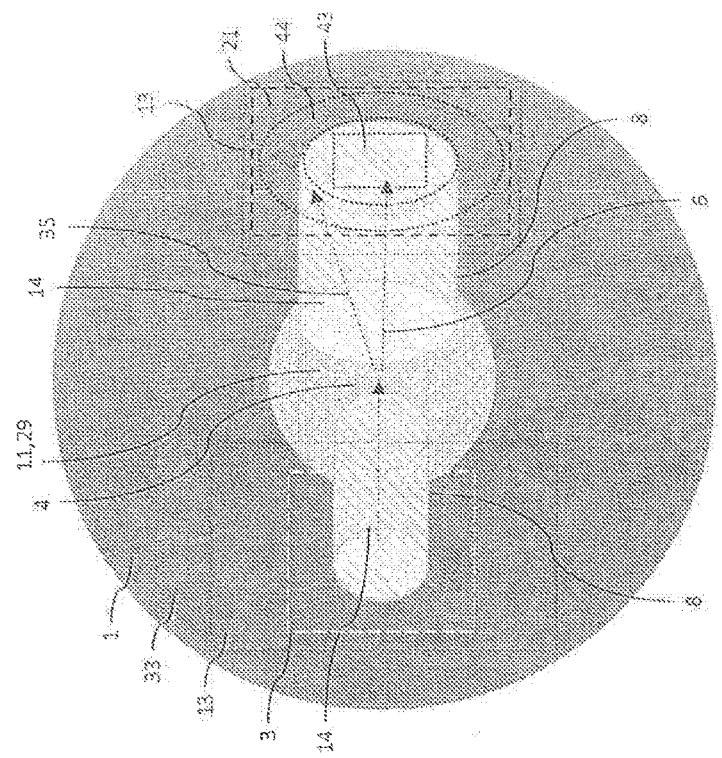
Figure 15B:
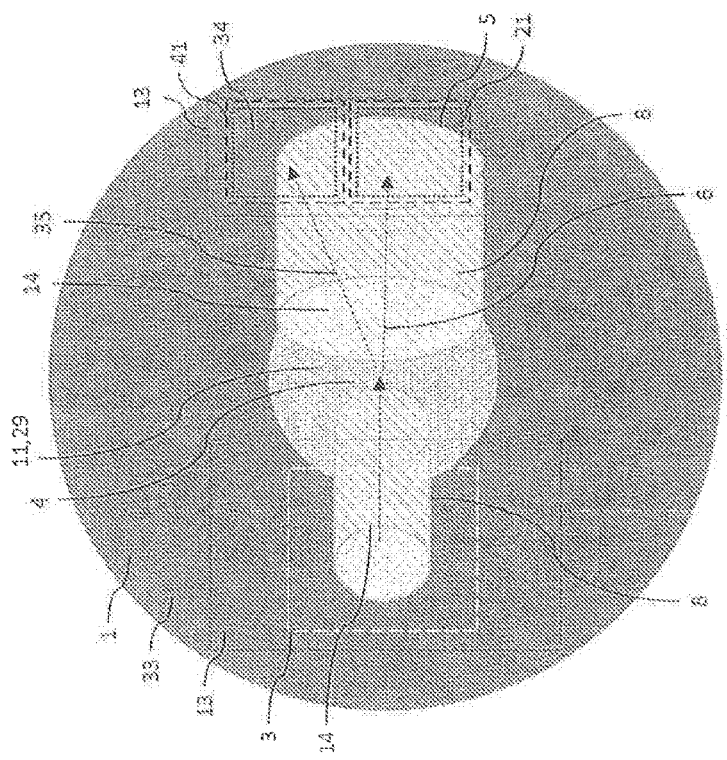

FIG. 15a-c Schematic cross-sectional and top-down views of still a further sensor embodiment with a detector comprising a single wavelength sensitive element and several detection surfaces.

Figure 16:
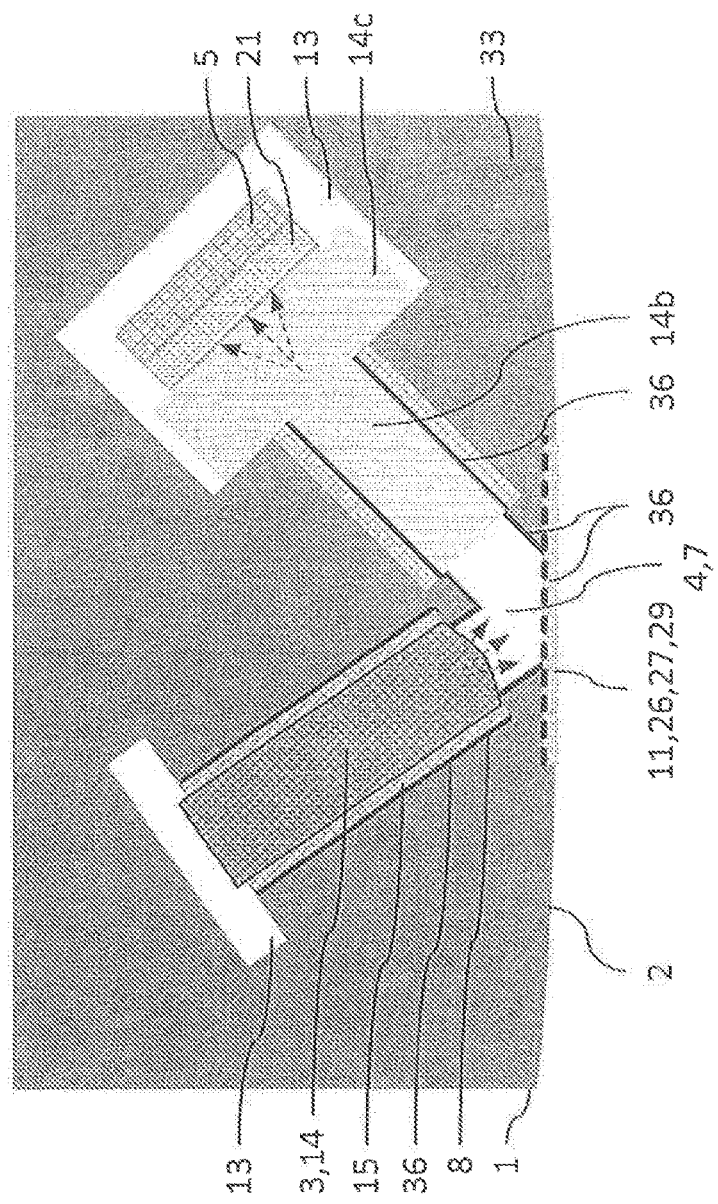

FIG. 16 A schematic cross-sectional view of a further sensor embodiment with a sealing element and a detector comprising a single wavelength sensitive element and at least two detection surfaces.

FIG. 17a-f Schematic cross-sectional views of a sensor detail, illustrating different implementations of a porous wall of the measurement volume with and without pore fillings.

FIG. 18a-e A schematic top-down view of four embodiments of a detector comprising a wavelength sensitive element and at least two detection surfaces.

FIG. 1 shows a schematic cross-sectional view of a sensor 1 for detection of gas. The sensor 1 comprises a contact face 2 which is directable towards a measuring site. In this case, the measuring site is an area on the skin of a patient and the gas to detect is $CO_2$ that has diffused through the skin of the patient, i.e. transcutaneously. The sensor furthermore comprises a radiation source 3 situated in a compartment 13, which emits radiation at least in a wavelength range where the radiation can be absorbed by the gas to be detected. Emitted radiation of suitable wavelength propagates along various paths 6 from the source 3 through a channel 8 comprising at least one sealing element 14 to the measurement volume 4, and from there through a further channel 8, also comprising a sealing element 14, through a wavelength filter 21 to a first detector 5, which is situated in a compartment 13. A certain fraction of the emitted radiation is absorbed by the gas to be detected in the measurement volume 4, depending on the concentration of the gas in the measurement volume 4. A change in absorption by the gas gives rise to a signal change from the detector 5, which allows inferring the gas concentration.

The detector 5 and the wavelength filter 21 can alternatively be replaced by a single detector comprising a first and a second detection surface (e.g. as illustrated in FIGS. 18a-e) and one common wavelength sensitive element such as an interference wavelength filter. The use of a detector having a second detection surface and a wavelength sensitive element enables to create a simpler and cheaper sensor that is easier to miniaturize and in addition can be more accurate.

The surfaces of the measurement volume 4, except the radiation entrance and exit openings, are predominantly highly reflective. The measurement volume 4 has no imaging purpose and any photon entering it performs a random walk. It is not crucial that the entering radiation has a specific spatial and radial intensity profile, as would be the case for imaging systems.

The shape of the measurement volume 4 is designed such that the upper surfaces directed towards radiation source 3 and first detector 5 form a planar surface. The surfaces of the sealing elements 14 form a part of that planar surface. Such a planar surface is created by roughly integrating cylindrical sealing elements 14 into a plate and, if necessary, additionally also a seal, followed by grinding and polishing until a planar surface is obtained. The other surface of the cylindrical sealing elements 14 is also planar and is created in the same way. Of course, planar surfaces can also be obtained by integration of sealing elements that are already of the appropriate shapes, without grinding and polishing.

Thus, two plate-like elements 40, one with a planar face and integrated sealing elements 14 and the other with a pit or depression extending from underneath one sealing element 14 to underneath the other, are joined such that the measurement volume 4 is formed by the two plate-like elements 40, consisting of the space confined by the planar face and the depression.

The gas to detect diffuses from the measurement site via contact face 2 and diffusion paths 26, which comprises contact pores 27 and an inner membrane 11, into the measurement volume 4. The first face of the inner membrane 11 forms at the same time a porous surface 30 of a permeable wall 29 of the measurement volume 4 and also is well reflecting, since it is made of an inherently reflecting material. Alternatively, the first surface of the inner membrane 11 has received a reflective layer 32. The inner membrane 11 is non-porous or porous with very small pore openings at the porous surface 30. The sizes of the pore openings at the porous surface 30 do not exceed about 1 µm. The second face of the inner membrane 11, is placed behind the contact face 2, where contact pores 27 form a connection between contact face 2 and second face of the inner membrane 11, such that gas molecules from the measurement site may access the measurement volume 4 by diffusion to and through the inner membrane 11, thus diffusion paths 26 lead through the inner membrane 11. Contact pores 26 may for example consist of small holes in the contact face 2 or sensor casing 33 or in a plate or film mounted such that it forms a contact face 2. Diffusion paths 26 for the gas molecules may then lead from the contact face 2 via contact pores 2 and inner membrane 11 to the measurement site 4.

Alternatively, the permeable wall 29 of the measurement volume 4 is not formed by the inner membrane but by a material comprising contact pores 27, for example small holes. The first face of that material, which is directed to the measurement volume, is reflective or is coated a reflective layer 32. The contact pores may extend to the contact face 2 or to near the contact face 2. The second face of that material comprising contact pores 27 can be adjacent to the inner face of an inner membrane 11, which may be porous or non-porous and whose outer face may form at least a part of the contact face 2. Diffusion paths 26 for the gas molecules may then lead from the contact face 2 via inner membrane 11 and contact pores 2 to the measurement site 4.

FIG. 2 shows a schematic cross-section of a sensor 1, comprising a radiation source 3 emitting measuring radiation, situated in a compartment 13. The measuring radiation propagates through a channel 8, comprising a non-cylindrical sealing element 14, into the measurement volume 4. The measuring radiation then propagates through the measurement volume 4 and at least one further channel 8, also comprising a non-cylindrical sealing element 14 and optionally a seal, passes through an NA converter 22 and a wavelength filter 21, finally impinging onto the first detector 5 situated in a compartment 13.

The gas to be measured can access the measurement volume 4 from the contact face 2 via gas diffusion paths 26 comprising contact pores 27 and an inner membrane 11. An outer membrane 10 is present on the contact face 2 at least during use. The sensor casing 33 has a receiving interface adapted for receiving the outer membrane 10 in a receiving position, such that, for example, the outer membrane can be clipped onto the sensor 1. The inner membrane 11 can extend from the contact face 2 into the sensor, where the inner face of the inner membrane 11 can form a permeable wall 29 of the measurement volume 4.

Alternatively, the inner face of the inner membrane 11 can be positioned at a distance from the measurement volume confinements, and diffusion paths 26 lead through a second permeable zone, consisting of small holes or contact pores 27 leading into the measurement volume 4. Furthermore, the inner membrane 11 is also positioned such that its outer face is at a distance from the contact face 2, and the inner membrane's 11 inner face is located at a distance from it. Diffusion paths 26 then lead additionally from the contact face through some further permeable zone, e.g. comprising contact pores 27, to the inner membrane 11.

The measurement volume 4 is a non-imaging optical element 7. It has predominantly reflective surfaces 36, except for those regions where measuring radiation ought to enter or leave the measurement volume 4. The measurement volume 4 is formed by two plate-like elements 40, where the element directed towards the measurement site is planar, apart from holes or pores enabling gas access. The second element comprises the channels 8 and sealing elements 14. A specific pit or depression in that second element, together with the planar face of the first element and the end faces of the sealing elements 14, forms the boundaries of the measurement volume 4. This allows radiation to propagate from the end face of one sealing element 14 to the end face of the other.

One of the main advantages of this embodiment is that the first plane-like element basically acts as a plane mirror, therewith it does not need to obtain a depression at a very well controlled site that is located exactly opposite the radiation entrance and exit positions. Hence, the tolerances for the first plate-like element can be relaxed, while those for the second need to be tight anyway.

FIG. 3 shows a schematic cross-section of a sensor 1, comprising a radiation source 3 emitting measuring radiation, situated in a compartment 13. The measuring radiation propagates along various radiation paths 6 through a channel 8, which comprises two spherical sealing elements 14a, into the measurement volume 4. The measuring radiation then propagates through the measurement volume 4 and a further channel 8, also comprising two spherical sealing elements 14a and optionally a further filling 9, further through an NA converter 22 and a wavelength filter 21, and finally impinges on the first detector 5 situated in the compartment 13. The channels 8 comprise reflective surfaces 36. Gas can access the measurement volume 4 through a porous or non-porous inner membrane 11, which extends from the contact face 2 to the measurement volume 4, in which case it would form a permeable wall 29 of the measurement volume with either good inherit reflectance or coated with a reflective layer 32.

The measurement volume 4 is formed from two plate-like elements 40, where the one directed to the measurement site is essentially planar. The other plate-like element contains the sealing elements 14a and a connecting pit, through which the measuring radiation propagates. The measurement volume 4 is non-imaging, thus represents a non-imaging optical element 7.

FIG. 4 shows a schematic cross-section of a sensor 1, comprising a radiation source 3 emitting measuring radiation, situated in a compartment 13. The measuring radiation propagates through a channel 8, which comprises a sealing element 14 and a seal 15, into the measurement volume 4. The measuring radiation then propagates through the measurement volume 4, which represents a non-imaging optical element 7, and through a further channel 8 comprising a sealing element 14 and a seal 15, through a wavelength filter 21, and finally impinges on the first detector 5 situated in a the compartment 13. The compartment is divided in two parts by a thermally and optically isolating wall. Either the channels 8 comprise reflective surfaces 36 and the seals 15 are at least reasonably transparent for measuring radiation, or the sealing elements 14 are coated by a reflective layer, such that there is no need for having reflective channels 8 or transparent seals 15.

The measurement volume 4 has a reflective surface 36 and is created by machining two or more meeting holes into a reflective material such as aluminum. This allows machining the measurement volume 4 from a single piece of material, such that there is no need for precise alignment of plate-like elements 40 forming the measurement volume.

Gas access to the measurement volume 4 is ensured by diffusion paths 26 through contact pores 27 and a gas collector comprising collecting channels 28. In an alternative embodiment the bottom of the measurement volume 4 is not formed by two meeting holes, but instead by a permeable wall consisting of an inner membrane 11 with reflective surface.

FIG. 5 shows a schematic cross-sectional drawing of a sensor detail, illustrating a possible implementation of a permeable wall 29 of the measurement volume 4. The permeable wall 29 is formed from an inner membrane 11, which has a porous surface 30 and has a reflective surface, for example due to a reflective layer 32 applied onto the surface. Pores 31 extend from the porous surface 30 to the contact face 2, such that gas molecules to be measured can diffuse along diffusion paths 26 from the contact face 2 through the inner membrane and the pores 31 into the measurement volume 4. The measurement volume 4 has reflective surfaces 36 substantially everywhere, except at the radiation entrance and exit surfaces, which are defined by spherical sealing elements 14a sealing a channel 8 with reflective surface 36.

FIG. 6 shows a schematic cross-sectional drawing of a sensor detail, illustrating a possible implementation of an inner membrane 11 comprising a gas-collection mechanism 12. The inner membrane 11 forms a permeable wall 29 of the measurement volume 4 and has a porous surface 30 as well as a reflective surface, for example due to a reflective layer 32 applied onto the porous surface 30. Pores 31 extend in the form of contact pores 27 from the porous surface 30 to the contact face 2 or to collecting channels 28, such that gas molecules to be measured can diffuse along diffusion paths 26 from the contact face 2 through collecting channels 28, through the inner membrane 11 and through the pores 31 into the measurement volume 4. The inner membrane 11 contains gas-permeable regions, for example collecting channels 28, diffusion paths 26 through contact pores 27, etc., but it can also contain gas-impermeable regions, which serve for maintaining the dimensional stability of the inner membrane 11 without providing gas-accessible volume that could slow down the sensor's response time.

The measurement volume 4 is confined also by irregularly shaped sealing elements 14 placed in the channels 8. The channels 8 can have a reflective surface 36 or the sealing elements 14 can be coated with a reflective layer. The collection area 24 of the gas collection mechanism is larger than the access area 25.

FIG. 7a,b show two schematic cross-sectional drawings of a sensor detail, illustrating how a spherical sealing element 14a (FIG. 7a) or a partially spherical sealing element 14a (FIG. 7b) and a seal 15 may be arranged to seal a channel 8. For example, the illustrated sensor detail may be located adjacent to a compartment 13, such that measuring radiation is transmitted through the spherical sealing element 14a into the channel 8, or such that measuring radiation is transmitted from the channel 8 through the spherical sealing element 14a into the compartment 13 towards a first detector. The channel 8 has reflective surfaces 36. Such a channel filling may be created by first bringing the spherical sealing element 14a to its intended location, for example by pressing, followed by filling the required part of the remaining space with e.g. a hardening and sealing liquid, thus forming the seal 15. The seal 15 ensures that the channel filling is leak tight, in case the spherical sealing element 14a alone would not be sealing tightly or reliably enough.

A partially spherical sealing element 14a is obtained from a spherical sealing element by flattening it with appropriate means, for example by grinding. The flattening treatment is preferably executed after application and hardening of the seal 15, especially if a fraction of the hardening sealing liquid can flow or be spilled onto the entire surface of the sphere, which is undesired unless the seal is highly transparent for measuring radiation.

FIG. 8a shows a schematic cross-sectional view of a sensor detail in the vicinity of the first detector 5. Radiation propagates from the radiation volume through the channel 8. The channel 8 comprises a filling 9, consisting of a sealing element 14 with a reflective surface 36 and a seal 15. Due to the non-imaging optical elements present along the radiation paths, for example the measurement volume, measuring radiation follows a variety of paths 6 upon leaving the channel filling 9. Radiation leaves the channel filling 9 at typically a broad angular distribution, which includes radiation leaving at high angles. Such high-angle radiation hits a wall of the NA converter 22, which has a reflective surface, and is reflected such that it impinges on the wavelength filter 21 at a low incidence angle. Without the NA converter 22, high-angle radiation would not be deflected and impinge on the wavelength filter 21 at significantly higher angle. Radiation transmitted through the wavelength filter 21 can reach the first detector 5 located in the compartment 13 and give rise to a measurement signal. Radiation leaving the channel filling 9 at low angles do not hit the NA converter 22 and impinge on the wavelength filter 21 without reflection. Thus, the NA converter narrows the angular spread of measuring radiation impinging on the wavelength filter 21 by converting high-angle to low-angle radiation, which improves the filter selectivity.

The NA converter 22 comprises a transparent filling 38. This transparent filling prevents gases from accessing the NA converter and thus the measurement result cannot be biased by changing concentrations of gases absorbing measuring radiation.

FIG. 8b shows an alternative embodiment, in which the NA converter 22 does not consist of a void created in a material, where the void may or may not comprise a transparent filling. Instead, the NA converter 22 is formed from a transparent part 39 having the shape of a transparent filling 38 completely filling the void of an NA converter 22. The transparent part 39 has a reflective coating 36 except on the radiation entrance and exit faces. Such an NA converter corresponds to an NA converter perfectly filled by a transparent filling 38 and is easier to integrate into the sensor.

FIG. 9 shows a schematic cross-sectional view of a sensor 1. The measurement volume 4 is connected with an environment 19 through an exchange channel 17. A water-permeable object 18, which is at the same time nearly or completely impermeable for the gas to measure contained in the measurement volume 4, is arranged in the exchange channel 17, close to the measurement volume 4. A reflecting element 20, which also is permeable for water molecules, is positioned in a part of the measurement volume wall. Thus, radiation propagating from the radiation source 3 via sealing element 14 into the measurement volume 4 will not enter the exchange channel 17 but instead remain in the measurement volume 4. This increases the amount of measuring radiation impinging on the detector, which in turn improves the measurement accuracy. Water molecules contained in the measurement volume 4 can access the water-permeable object 18 through the reflecting element 20 and diffuse to the environment 19. In this way, the gas mixture in the measurement volume 4 is kept sufficiently dry such that no condensation of liquid water can occur.

FIG. 10 shows a schematic cross-sectional view of a sensor 1. The measurement volume 4 is connected to an exchange channel 17. A water trap 16, which is preferably nearly or completely impermeable for the gas to measure contained in the measurement volume 4, is arranged in the exchange channel 17, close to the measurement volume 4. A reflecting element 20, which also is permeable for water molecules, is positioned in a part of the measurement volume wall. Thus, radiation propagating from the radiation source 3 via sealing element 14 into the measurement volume 4 will not enter the exchange channel 17 but instead remain in the measurement volume 4. This increases the amount of measuring radiation impinging on the detector, which in turn improves the measurement accuracy. Water molecules contained in the measurement volume 4 can access the water trap 16 through the reflecting element 20 and become trapped in the water trap 16. In this way, the gas mixture in the measurement volume 4 is kept sufficiently dry such that no condensation of liquid water can occur.

FIGS. 11a,b,c show a schematic cross-sectional drawing of a detail of a sensor 1, illustrating the vicinity of the measurement volume 4 and three possible arrangements of water traps 16 in a disposable part of the sensor 1. The measurement volume 4 is formed by two plate-like elements 40, where one of the plate-like elements 40 is substantially planar. The measurement volume 4 comprises a permeable wall 29, which is formed by an inner membrane 11. Molecules present at the measurement site can diffuse via diffusion paths 26 into the measurement volume 4. The inner membrane 11 is permeable for water molecules, such that water molecules contained in the measurement volume 4 can diffuse through the inner membrane 11 and reach one or several water traps 16, where they can become trapped. This keeps the gas mixture contained in the measurement volume 4 sufficiently dry, such that no liquid water can condense in the measurement volume 4. Furthermore, water molecules can also reach the water traps 16 directly, i.e., without visiting the measurement volume 4, for example by diffusion along the contact face 2 of the sensor 1, by diffusion through the outer membrane 10 at the locations of the water traps 16, or via diffusion paths 26, particularly when diffusion paths 26 lead through contact pores 27 existing in the water trap 16 material.

The water traps 16 are suitably combined with the outer membrane 10, such that replacement of the outer membrane also replaces the water traps 16. In this way, fresh water traps 16 can easily be installed in the sensor 1.

FIGS. 12a,b show a detailed view of and onto the contact face 2 of a sensor 1, indicating the access area 25 in the absence (FIG. 12a) and the access area 25 and the collection area 24 in the presence (FIG. 12b) of a gas collector 23.

In the absence of a gas collector 23, as shown in FIG. 12a, gas molecules present at the contact face 2 within the access area 25 can efficiently access a contact pore 27 and diffuse into the measurement volume via diffusion paths.

Figure 12B:
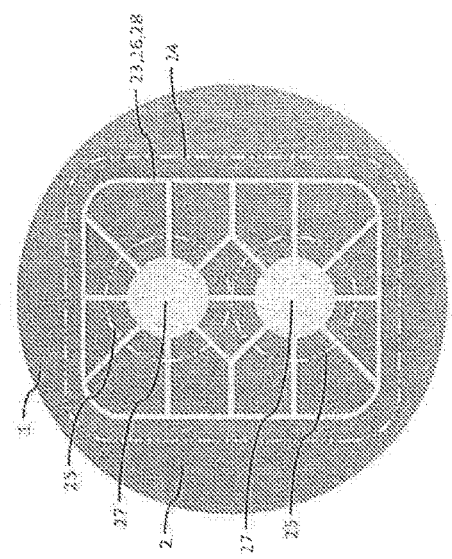

In the presence of a gas collector 23, as shown in FIG. 12b, gas molecules present at the contact face 2 within the collection area 24 can efficiently access a contact pore 27 or the gas collector 23. Once in the gas collector 23, gas molecules can diffuse along collecting channels 28 and further diffusion paths 26 in the gas collector 23, such as scratches or holes, into the contact pore 27 and from there further on into the measurement volume.

Thus, the gas collector 23 increases the zone from which gas molecules can efficiently access the diffusion paths leading to the measurement volume, which shortens the response time of the sensor.

FIG. 13 shows a schematic top-down view of a sensor 1 and through that sensor 1, illustrating how measuring radiation propagates along a path 6 from the radiation source 3, which is located in a compartment 13, through a sealing element 14 filling a channel 8 into the measurement volume 4 and from there through a further sealing element 14 filling a channel 8 and through a wavelength filter 21 to a first detector 5, located in the compartment 13. Furthermore, measuring radiation is also propagating along a second path 35 through the measurement volume 4, through yet a further sealing element 14 filling a further channel 8, and through a second wavelength filter 41 having a different nominal passband than the wavelength filter 21 to the second detector 34 located in a compartment 13. Alternatively, instead of a first detector 5 and a second detector 34, each with a wavelength filter 21, a detector comprising two detection surfaces and a single wavelength sensitive element as shown in FIG. 18a-e can be used.

Gas molecules from the measurement site can access the measurement volume 4 through contact pores 27. The sensor casing 33 is gas tight such that no gas from the environment or the measurement volume 4 can access or leave the compartments 13 and lead to a biased measurement.

FIGS. 14a and 14b show schematic cross-sectional and top-down views of a sensor 1, respectively.

FIGS. 14a and 14b illustrate an embodiment of a sensor 1 of a similar kind as previously described, but with the following distinct features. Measuring radiation rays propagate from the source 3 along optical paths 6 within a common beam firstly through a first sealing element 14 in a channel 8, then through the measurement volume 4 and thereafter through a second sealing element 14 in a channel 8 (right hand side of FIG. 14a). Instead of integrating one sealing element 14 into the channel 8 it is also conceivable to integrate several sealing elements into the channel 8. Furthermore, the sealing element 14 may also protrude from the channel 8, as indicated in the cross-sectional drawing, and may have a reflective outer surface 36. Radiation propagates in a common beam until it leaves the last channel 8 or the last sealing element 14 on its path, whichever comes last.

Thereafter, the radiation beam enters an NA converter 22, which is a beam splitting NA converter and which additionally can comprise a transparent filling. The radiation beam is split up into two individual beams only after entering the beam splitting NA converter 22. Such a design makes the sensor robust against changes in reflective properties particularly in the measurement chamber, e.g. due to corrosion, contamination or condensation; furthermore, the measurement volume can be small. The two individual radiation beams are directed onto a first wavelength filter 21 and from there reach a first detector 5 and onto a second wavelength filter 41 and from there reach a second detector 34, respectively (see FIG. 14*b*). Therewith, measuring radiation of a first wavelength can be guided along the optical path 6 and detected by a first detector 5, while measuring radiation of a second wavelength can be guided along a second optical path 35 and detected by a second detector 34.

The measurement volume 4 in this embodiment is defined by two meeting, angled holes, and a permeable wall 29 with a reflective surface or coating 36 as a bottom reflector, together forming a non-imaging optical element 7. The permeable wall 29 at the same time serves as an inner membrane having contact pores 27 serving as diffusion paths 26 for measuring gas present near the sensor's contact face 2.

FIG. 15*a* shows a schematic cross-sectional and FIGS. 15*b,c* show schematic top-down views of an alternative sensor 1. This embodiment is similar to the one illustrated in FIGS. 14*a,b* except for the following distinct features. The sealing element 14 between the measurement volume 4 and the detector compartment 13 is relatively wide. This leads to a broadening radiation beam, where measuring radiation of all wavelengths is similarly distributed within the beam. However, the angular distribution of the rays within the beam is not uniform; rays leaving the sealing element 14 near the center have a lower angle relative to the surface normal of the sealing element than rays leaving the sealing element off-center.

This is advantageous for detection of measuring radiation when placing, as indicated in FIG. 15*b*, a first detector 5 and a second detector 34 with a first 21 and a second 41 wavelength filter, respectively, onto the sealing element 14 surface, where a small gap between sealing element and wavelength filters may exist.

Alternatively, as indicated in FIG. 15*c*, a detector comprising a single wavelength sensitive element 21 and a first 43 and a second 44 detection surface can be arranged near the exit surface of the sealing element 14. The first 43 and second 44 detection surfaces can have shapes for example as illustrated in FIGS. 18*a-d*, and can be arranged concentrically, for example.

In such a design, measurement radiation passes only through very short sections of gas-accessible space, apart from the measurement volume. Therefore, any gas to be measured that has reached the compartment 13 of the detector cannot significantly bias the measurement result of the gas to be measured in the measurement volume 4. This keeps the sensor measuring accurately even when leaks in the channel seals 15 should exist.

FIG. 16 shows a similar embodiment of a sensor 1 as in FIGS. 15*a-c* except for two main features. The first is a radiation source 3 which at the same time is also used as a sealing element 14. Radiation is injected into the measurement volume efficiently, and a reflective surface 36 of the channel 8 or of the sides of source 3 can further help to increase the injected radiation intensity. Furthermore, no separate sealing element is required and by design there cannot by any gas-accessible space between sealing element and source which could lead to a biased measurement result in case that gas-accessible space contains gas to be measured. The second main feature is that there is no single wide sealing element 14 as in FIGS. 15*a-c* but instead a narrower sealing element 14*b*, for example with a reflective coating 36, and on top a further sealing element 14*c* that is wider and allows the radiation beam to widen as in the embodiment of FIGS. 15*a-c*. With this method, it is easier to keep the measurement volume small.

FIG. 17*a* shows a more detailed view of a measurement volume 4 bottom. The sensor 1 comprises a sensor casing 33 with two channels 8. Sealing elements 14 comprising a reflective surface 36 are arranged in the channel 8 and sealed by an additional seal 15. Gas to be measured can access the measurement volume from contact face 2 through contact pores 27, diffusion paths 26, a permeable wall 29, and pores 31 into measurement volume 4. The measurement volume, including the permeable wall 29, comprises reflective surfaces 36. The permeable wall 29 can serve as an inner membrane 11 at the same time. An outer membrane 10 may be present during use or constantly.

Alternatively it may be omitted. In case an additional outer membrane (not shown) is present only during use, for example an outer membrane integrated into a disposable device as for example a patient applicator as referred to above, an outer membrane attached to the sensor becomes an intermediate membrane 45, since during a measurement on a patient's skin in total three membranes are present.

FIG. 17*b* shows all features of FIG. 17*a* with an additional pore filling 42 in pores 31.

FIG. 17*c* differs from FIG. 17*a* in that a permeable wall 29 with less but wider pores 31 having a diameter of at least 0.01 mm and up to 0.5 mm and reflective surface 36 is used, where the locations of the wide pores 31 need to be well chosen to avoid excessive loss of measuring radiation through them.

FIG. 17*d* shows all features of FIG. 17*c* with an additional pore filling 42 in the wide pores 31, which is particularly useful in this case, since contamination can more easily access the measurement volume 4 through wider pores 31 than through narrower pores.

FIG. 17*e* shows a combination of FIGS. 17*a* and 17*c*. A permeable wall 29*a* of the measurement volume 4 can have narrow pores and a reflective surface 36 and at the same time serve as inner membrane 11. A second, outer permeable wall 29*b* having wider pores arranged in contact with or very close to the first permeable wall 29*a* can at the same time serve as an outer membrane 10. In case an additional outer membrane (not shown) is present only during use, for example an outer membrane integrated into a disposable device as for example a patient applicator as referred to above, the outer permeable wall 29*b* can serve as an intermediate membrane 45.

FIG. 17*f* shows all features of FIG. 17*e* with an additional pore filling 42 in the wide pores 31 of the outer permeable wall 29*b*. This creates a contact face 2 of the sensor that has no unfilled openings towards the measurement volume 4.

FIGS. 18*a-e* show detailed schematic views of a preferred embodiment of a detector 5. The detector 5 comprises a first detection surface 43 for detection of radiation in a first wavelength band and at least a second detection surface 44 for detection of radiation in a second wavelength band. The detector is provided with a wavelength sensitive element formed by an interference wavelength filter 21. Not shown are electrical contacts to the detection surfaces, which are required for electrical collection of the measurement signal generated by the detection surfaces 43 and 44, and a common support, where detection surfaces and wavelength filter are arranged on. This detector preferably is used in a sensor as described herein above with reference to e.g. FIG. 15c.

FIG. 18a illustrates an implementation with a round first detection surface 43 and a substantially surrounding, concentric, substantially ring-shaped peripheral second detection surface 44, both located underneath a single interference wavelength filter 21. Both detection surfaces 43, 44 are arranged at a distance from each other and are electrically separated. The gap between the two detection surfaces 43 and 44 is used for routing electrical contacts through. It furthermore gives rise to a better separation of the radiation wavelength bands detectable by the detection surfaces 43 and 44.

FIG. 18b shows all features of FIG. 18a, except that the first detection surface 43 is square instead of circular.

FIG. 18c basically shows the same features as FIG. 18a, except that the second detection surface 44 only consists of two sections of a ring located to each side of the first detection surface 43. The two second detection surfaces 44 for example can be connected in parallel, such that their signals are averaged, which is particularly advantageous when the detector 5 is arranged such that the two second detection surfaces 44 are sensitive to radiation of the same wavelength band. The ring-shaped second detection surface 44 of FIG. 18a potentially can collect more radiation than the two second detection surfaces 44 of FIG. 18c, but it also requires more space and therefore is less easily miniaturized.

FIG. 18d shows all features of FIG. 18c, except that the first detection surface 43 is square instead of circular and that the second detection surfaces 44 are also rectangular. Such shapes can be easier to connect with electrical contacts.

FIG. 18e shows the features of FIG. 18d, except that one of the two second detection surfaces 44 is omitted. The first 43 and second 44 detection surfaces are not concentric anymore in this embodiment, but the detector 5 is arranged still such that radiation of a first and second range of incidence angles and in a first and second wavelength band reaches the first and second detection surface 43 and 44, respectively, as in the other embodiments sketched in FIGS. 18a-d. This results in the first detection surface 43 being located centrally, while the second detection surface 44 is located peripherally, with respect to the radiation beam. Hence, compared to FIG. 18d, with the design of FIG. 18e less radiation in the second wavelength band can be detected by a second detection surface 44, but in return the detector can be made even more compact.

The invention claimed is:

1. A sensor for detection of transcutaneous gas comprising a contact face which is configured to be directed towards a measuring site and the sensor further including at least one gas diffusion path, at least one radiation source for emission of measuring radiation, a measurement volume for receiving the gas to be measured, and a detector for detection of electromagnetic radiation, said detector comprising at least a first detection surface and a second detection surface and at least one wavelength sensitive element,
    wherein the wavelength sensitive element is substantially transparent for radiation of wavelengths in a first wavelength band incident onto the wavelength sensitive element in a first range of incidence angles and for radiation of wavelengths in a second wavelength band incident onto the wavelength sensitive element in a second range of incidence angles, the first and the second wavelength bands are at least partly different from each other, and the first and the second ranges of incidence angles are at least partly different from each other, the first detection surface and the second detection surface and the at least one wavelength sensitive element are arranged such that radiation in the first wavelength band propagates through the wavelength sensitive element such that the radiation in the first wavelength band impinges on said first detection surface and is detectable by said first detection surface and such that radiation of the second wavelength band propagates through the wavelength sensitive element such that the radiation of the second wavelength band impinges on said second detection surface and is detectable by said second detection surface.

2. The detector sensor according to claim 1, wherein the second detection surface is arranged concentrically with respect to the first detection surface.

3. The detector sensor according to claim 1, wherein the second detection surface at least partly surrounds the first detection surface.

4. The detector sensor according to claim 1, wherein said detector comprises exactly two detection surfaces.

5. The detector sensor according to claim 1, wherein the first and the second detection surface are arranged on a common support.

6. The sensor according to claim 1, wherein the detector is arranged such that radiation in said first and said second wavelength bands are detectable by said first and second detection surfaces when measuring radiation is propagating within said sensor along a multitude of different optical paths from the radiation source through said measurement volume towards said detector and the rays of said measuring radiation are distinctly divergent when they impinge on said wavelength sensitive element.

7. The sensor according to claim 1, wherein the detector is arranged such that if measuring radiation rays of different wavelengths are propagating within a common beam towards the wavelength sensitive element, the rays in different wavelength bands only propagate within separate beams after entering the wavelength sensitive element to said first and second detection surface.

8. The sensor according to claim 1, wherein the radiation source is a thermal radiator.

9. The sensor according to claim 1, wherein the radiation source comprises an infrared LED.

10. The sensor according to claim 1, wherein a sensor casing is gas-tight.

11. The sensor according to claim 1, wherein the radiation source comprises an infrared laser.

12. The sensor according to claim 1, wherein radiation at least in a range between 1 and 12 μm is detectable by a first detector.

13. The sensor according to claim 1, wherein the measuring volume has a volume less than 10 mm$^3$.

14. The sensor according to claim 1, wherein the sensor comprises a second detector and a second path between measurement volume and the second detector.

15. The sensor according to claim 14, wherein the second path is at least partially separated from a path between a first detector and the measurement volume.

16. The sensor according to claim 1, comprising a pore filling.

17. The sensor according to claim 1, wherein the sensor without communication and power supply means fits into a virtual cylinder having a diameter of 30 mm and a height of 20 mm or into a virtual volume of 15 cm$^3$.

18. The sensor according to claim 1, wherein the sensor comprises a communication interface that only communicates with other devices by electric or electronic means.

19. The sensor according to claim 1, wherein the total length of the shortest complete optical path from said source via said measurement volume to said detector or said detection surfaces does not exceed 20 mm.

20. The sensor according to claim 1, wherein a sum of the lengths of those sections of the shortest complete optical path from said source via said measurement volume to said detector or said detection surfaces, that lead through gas-accessible volumes other than said measurement volume, does not exceed 3 mm.

21. The sensor according to claim 1, wherein the average electrical power delivered to the sensor is below 5 W.

22. The sensor according to claim 1, wherein the first detection surface and the second detection surface are arranged behind the contact surface.

23. The sensor according to claim 22, wherein the first and the second detection surfaces are not arranged besides the contact surface or wherein the first and the second detection surfaces are not arranged with a lateral offset with respect to the contact surface.

24. The sensor according to claim 1, wherein the at least one gas diffusion path extends through a membrane for protecting the measurement volume, which membrane during use is to be placed on the measurement site, which is on the skin of a human or animal subject.

25. The sensor according to claim 1, wherein the detector for detection of electromagnetic radiation is arranged for receiving only measuring radiation that was reflected at least once within the measuring volume.

26. The sensor according to claim 1, wherein the sensor comprises at least one seal, which is arranged such that the measuring radiation propagates through the seal.

* * * * *